United States Patent
Klintz et al.

[11] Patent Number: 6,013,606
[45] Date of Patent: Jan. 11, 2000

[54] SUBSTITUTED CINNAMIC OXIME AND HYDROXAMIDE DERIVATIVES

[75] Inventors: Ralf Klintz, Gruenstadt; Gerhard Hamprecht, Weinheim; Elisabeth Heistracher, Ludwigshafen; Peter Schäfer, Ottersheim; Christoph-Sweder von dem Bussche-Hünnefeld, Mannheim; Peter Münster, Römerberg; Reinhard Kirstgen, Neustadt; Albrecht Harreus, Ludwigshafen; Karl-Otto Westphalen, Speyer; Matthias Gerber, Limburgerhof; Helmut Walter, Obrigheim, all of Germany

[73] Assignee: BASF Akteingesellschaft, Ludwigshafen, Germany

[21] Appl. No.: 08/765,180

[22] PCT Filed: Jul. 4, 1995

[86] PCT No.: PCT/EP95/02584

§ 371 Date: Jun. 30, 1997

§ 102(e) Date: Jun. 30, 1997

[87] PCT Pub. No.: WO96/02518

PCT Pub. Date: Feb. 1, 1996

[30] Foreign Application Priority Data

Jul. 14, 1994 [DE] Germany .............................. 44 24 791

[51] Int. Cl.$^7$ .......................... A01N 43/54; A01N 43/50; C07D 223/10; C07D 235/26
[52] U.S. Cl. .......................... 504/223; 504/166; 504/168; 504/219; 504/243; 504/286; 540/601; 540/529; 544/65; 544/312; 548/513; 558/391; 560/17; 560/22; 560/32; 560/18; 560/35; 560/135; 560/136; 560/358; 564/256; 564/265
[58] Field of Search .................................... 504/166, 168, 504/219, 223, 243, 286; 540/601, 529; 544/65, 312; 548/513; 558/391; 560/17, 22, 32, 35, 18, 135, 136, 358; 564/256, 265

[56] References Cited

U.S. PATENT DOCUMENTS

| | | | |
|---|---|---|---|
| 4,979,982 | 12/1990 | Brouwer et al. | 71/92 |
| 4,990,174 | 2/1991 | Rueb et al. | 71/92 |
| 5,009,701 | 4/1991 | Plath et al. | 71/96 |
| 5,017,211 | 5/1991 | Wenger et al. | 71/92 |
| 5,035,740 | 7/1991 | Poss | 71/93 |
| 5,045,105 | 9/1991 | Grossmann et al. | 71/74 |
| 5,336,663 | 8/1994 | Wenger et al. | 504/243 |

FOREIGN PATENT DOCUMENTS

| | | |
|---|---|---|
| 0289910 | 11/1988 | European Pat. Off. |
| 408 382 | 9/1996 | European Pat. Off. |
| 90/02120 | 3/1990 | WIPO |
| 93/06090 | 4/1993 | WIPO |
| 93/11669 | 6/1993 | WIPO |

OTHER PUBLICATIONS

Chem. Abst., vol. 105, No. 7, 1986, Abst. No. 60524v.

Primary Examiner—Peter O'Sullivan
Assistant Examiner—Taylor V. Oh
Attorney, Agent, or Firm—Keil & Weinkauf

[57] ABSTRACT

Substituted cinnamic oxime derivatives I and cinnamic hydroxamide derivatives II

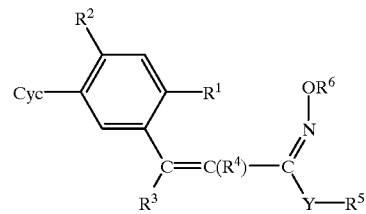

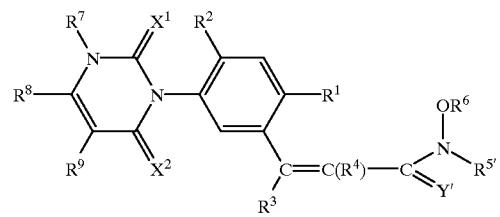

($R^1$=halogen, $NO_2$, CN, $CF_3$; $R^2$=H, halogen;

$R^3$=H, halogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl;

$R^4$=H, halogen, CN, $C_1$–$C_6$-alkyl, $C_1$–$C_6$-haloalkyl or $R^3$+$R^4$=chemical bond;

Y=—O—, —S—, —O—CO—, —O—$SO_2$— or chemical bond;

Y'=—O— or —S—;

$R^5$=unsubst. or subst. $C_1$–$C_6$-alkyl or $C_1$–$C_6$-haloalkyl; $C_3$–$C_6$-cycloalkyl, $C_3$–$C_6$-alkenyl, $C_3$–$C_6$-alkynyl, unsubst. or subst. phenyl or phenyl-$C_1$–$C_6$-alkyl, or, if Y is —O—, —S— or a chemical bond, is ($C_1$–$C_6$-alkyl)carbonyl or ($C_1$–$C_6$-alkoxy)carbonyl; or, if Y is a chemical bond, is hydrogen or halogen;

$R^{5'}$=$R^5$, H or ($C_1$–$C_6$-haloalkyl)carbonyl;

$R^6$=H, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkoxy) carbonyl-$C_1$–$C_6$-alkyl, ($C_1$–$C_6$-alkyl) carbonyl-$C_1$–$C_6$-alkyl, ($C_1$–$C_6$-alkyl)carbonyloxy-$C_1$–$C_6$-alkyl or unsubst. or subst. phenyl-$C_1$–$C_6$-alkyl;

or, if Y is oxygen or sulfur, $R^5$+$R^6$ together=unsubst. or subst. $C_1$–$C_3$-alkylene;

Cyc=N-(3,4,5,6-tetrahydrophthalimido) or
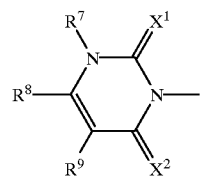
$X^1$, $X^2$=oxygen or sulfur;
$R^7$=H, $C_1$–$C_6$-alkyl, $C_1$–$C_6$-haloalkyl, $NH_2$;
$R^8$, $R^9$=H, halogen, $C_1$–$C_6$-alkyl, $C_1$–$C_6$-haloalkyl or unsubst. or subst. phenyl);
and salts of I and II.
Use: herbicides; desiccation/defoliation of plants.
17 Claims, No Drawings

SUBSTITUTED CINNAMIC OXIME AND HYDROXAMIDE DERIVATIVES

The present invention relates to novel substituted cinnamic oxime derivatives of the formula I

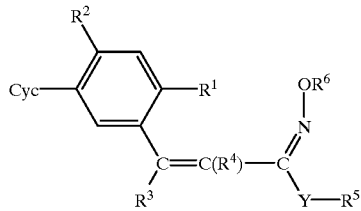

where the variables have the following meanings:

$R^1$ is halogen, nitro, cyano or trifluoromethyl;

$R^2$ is hydrogen or halogen;

$R^3$ is hydrogen, halogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl or hydroxy-$C_1$–$C_6$-alkyl;

$R^4$ is hydrogen, halogen, cyano, $C_1$–$C_6$-alkyl, $C_1$–$C_6$-haloalkyl, or $R^3$ and $R^4$ together are a chemical bond;

Y is oxygen, sulfur, oxycarbonyl, oxysulfonyl or a chemical bond;

$R^5$ is $C_1$–$C_6$-alkyl or $C_1$–$C_6$-haloalkyl, it being possible for these groups to be unsubstituted or to carry one of the following radicals: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)-carbonyl, ($C_1$–$C_6$-alkyl)carbonyloxy or a 3- to 7-membered azaheterocycle bonded to the nitrogen atom via a carbonyl bridge and which, in addition to carbon ring members, can also contain an oxygen or sulfur atom as a ring member;

is $C_3$–$C_6$-cycloalkyl, $C_3$–$C_6$-alkenyl, $C_3$–$C_6$-alkynyl, phenyl or phenyl-$C_1$–$C_6$-alkyl, it being possible for the phenyl rings, if desired, to carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

or, if Y is oxygen, sulfur or a chemical bond, is ($C_1$–$C_6$-alkyl)carbonyl, ($C_1$–$C_6$-alkoxy)carbonyl;

or, if Y is a chemical bond, is hydrogen or halogen;

$R^6$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkoxy)carbonyl-$C_1$–$C_6$-alkyl, ($C_1$–$C_6$-alkyl)carbonyl-$C_1$–$C_6$-alkyl, ($C_1$–$C_6$-alkyl)carbonyloxy-$C_1$–$C_6$-alkyl or phenyl-$C_1$–$C_6$-alkyl, it being possible for the phenyl ring, if desired, to carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy) carbonyl;

or, if Y is oxygen or sulfur, $R^5$ and $R^6$ together are a $C_1$–$C_3$-alkylene chain which can carry a $C_1$–$C_6$-alkyl substituent;

Cyc is N-(3,4,5,6-tetrahydrophthalimido) or a radical

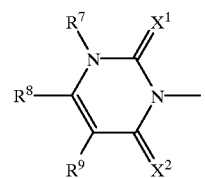

$X^1$ and $X^2$ independently of one another being oxygen or sulfur;

$R^7$ being hydrogen, $C_1$–$C_6$-alkyl, $C_1$–$C_6$-haloalkyl or amino and $R^8$ and $R^9$ independently of one another being hydrogen, halogen, $C_1$–$C_6$-alkyl, $C_1$–$C_6$-haloalkyl or phenyl which, if desired, can carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

and the agriculturally utilizable salts of the compounds I, if these exist.

The invention additionally relates to novel substituted cinnamic hydroxamide derivatives of the formula II

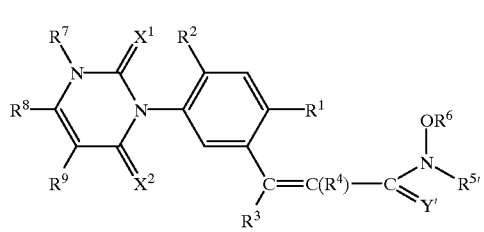

where the variables $R^1$, $R^2$, $R^3$, $R^4$, $R^6$, $R^7$, $R^8$, $R^9$, $X^1$ and $X^2$ have the same meanings as in the compounds of the formula I and in which $R^{5'}$ is hydrogen, $C_1$–$C_6$-alkyl or $C_1$–$C_6$-haloalkyl, it being possible for the last two groups to carry one of the following radicals: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy or a 3- to 7-membered azaheterocycle bonded to the nitrogen atom via a carbonyl bridge and which, in addition to carbon ring members, can also contain an oxygen or sulfur atom as a ring member;

is $C_3$–$C_6$-cycloalkyl, $C_3$–$C_6$-alkenyl, $C_3$–$C_6$-alkynyl, ($C_1$–$C_6$-alkyl)carbonyl, ($C_1$–$C_6$-haloalkyl)carbonyl, ($C_1$–$C_6$-alkoxy) carbonyl;

is phenyl or phenyl-$C_1$–$C_6$-alkyl, it being possible for the phenyl rings, if desired, to carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)-carbonyl; and Y' is oxygen or sulfur.

In addition, the invention relates to the use of the compounds I or II as herbicides and for the desiccation and/or defoliation of plants, herbicidal compositions and compositions for the desiccation and/or defoliation of plants, which contain the compounds I or II as active substances, processes for preparing these herbicidal compositions and compositions for the desiccation and/or defoliation of plants, processes for controlling undesired plant growth and for the desiccation and/or defoliation of plants using the compounds I or II, and also novel intermediates of the formula IX for preparing the compounds I.

EP-A-0 385 231 discloses that, inter alia, compounds of the formula IIIa

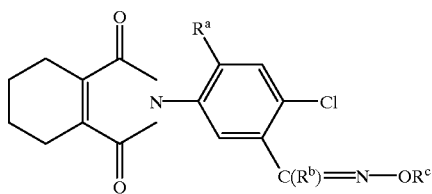

where $R^a$ is hydrogen, fluorine or chlorine, $R^b$ is hydrogen or cyano and $R^c$ is $C_1$–$C_6$-alkyl, $C_3$–$C_4$-alkenyl, $C_3$–$C_4$-alkynyl, —$CH_2$—COOH, —CH($CH_3$)—COOH, —$CH_2$—C($CH_3$)$_2$—COOH, —$CH_2$-ester, —CH($CH_3$)-ester or —$CH_2$—C($CH_3$)$_2$-ester, are suitable for the desiccation and abscission of parts of plants.

It is additionally related in JP-A 61/027962 that compounds of the formula IIIb

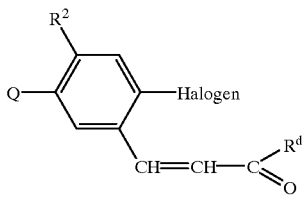

where Q is N-(3,4,5,6-tetrahydrophthalimido)- or

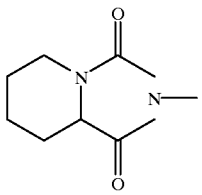

and $R^d$, inter alia, is the amino group, which can carry certain substituents, are herbicidally active.

EP-A-0 358 108 describes compounds of the formula IIIc

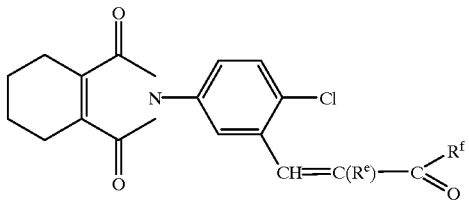

where $R^e$ is chlorine, bromine or $C_1$–$C_4$-alkyl and $R^f$, inter alia, is a mono- or disubstituted amino group.

It can additionally be inferred from U.S. Pat. No. 5,035,740 that certain N-phenylazaheterocycles whose phenyl ring carries in the 2-position to the heterocycle, inter alia, a radical $R^2$, in the 4-position to the heterocycle, inter alia, a hydrogen or halogen atom or a haloalkyl radical, and in the 5-position to the heterocycle, inter alia, an unsubstituted or substituted 2-(aminocarbonyl)ethenyl group, are herbicidally active.

EP-A-0 379 911 describes as herbicides N-phenyltetrahydroindazole derivatives of the formula IIId

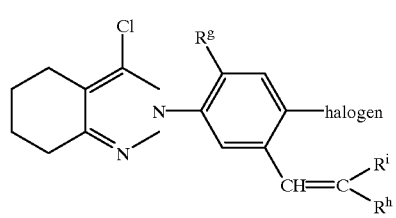

where $R^g$ is hydrogen or fluorine, $R^h$ is hydrogen, halogen or $C_1$–$C_4$-alkyl and $R^i$, inter alia, is an acid amide radical.

WO 90/02120 discloses that certain 1-phenyl-4,5-dihydro-1,2,4-triazol-5-(1H)-ones whose phenyl ring carries in the meta-position to the heterocycle, inter alia, an unsubstituted or substituted 2-(aminocarbonyl)ethenyl group, show herbicidal action.

U.S. Pat. No. 4,979,982 additionally discloses herbicidally active 3-phenyluracils of the formula IIIe

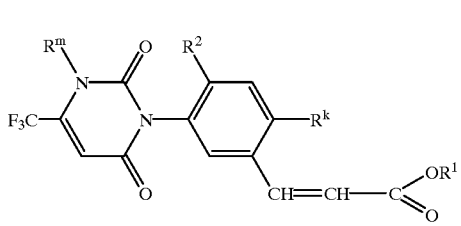

$R^k$ being hydrogen or halogen, $R^l$ being $C_1$–$C_{12}$-alkyl or cycloalkyl and $R^m$ being $C_1$–$C_{12}$-alkyl or $C_3$–$C_{12}$-alkenyl.

Herbicides structurally similar to the compounds IIIb are additionally described in WO 93/06090.

It can be inferred from EP-A 408 382 that, inter alia, uracil derivatives of the formula IIIf

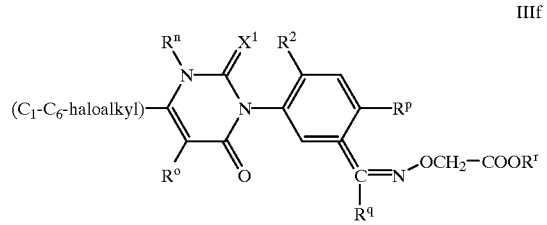

$R^n$ being hydrogen, hydroxymethyl or $C_1$–$C_3$-[halo]alkyl, $R^o$ being hydrogen, nitro, halogen, $C_1$–$C_6$-[halo]alkyl or hydroxymethyl, $R^p$ being nitro, cyano or halogen, $R^q$ being hydrogen, $C_1$–$C_3$-alkyl, -alkoxy or -alkoxy-$C_1$–$C_2$-alkyl and $R^r$ being hydrogen, $C_1$–$C_4$-alkyl, $C_2$–$C_3$-haloalkyl, $C_3$–$C_6$-cycloalkyl, phenyl or benzyl, have a herbicidal action.

According to WO 89/02891, certain 3-(3-aminocarbonylphenyl)-uracils are also herbicidally active.

Finally, it is related in WO 93/11669 that certain 3-(3-aminocarbonyl)uracils are suitable for the desiccation and abscission of plant organs.

As the selectivity of the known herbicides in relation to the weeds may only be satisfactory to a limited extent, it is an object of the present invention to provide herbicidally active compounds with which, with good tolerability for the crop plants, the weeds can be specifically controlled better than previously.

We have found that this object is achieved by the substituted cinnamic oxime derivatives of the formula I. Novel compounds of the formula II were additionally found, which are useful intermediates for the synthesis of the compounds I or are obtained during their preparation as by-products.

In addition, herbicidal compositions were found which contain the compounds I or II and have a very good herbicidal action. Processes for preparing these compositions and methods for controlling undesired plant growth using the compounds I or II were additionally found.

The compounds I and II according to the invention are additionally suitable for the defoliation and desiccation of parts of plants in eg. cotton, potatoes, rape, sunflowers, soybeans or field beans, in particular in cotton. With respect to this, compositions for the desiccation and/or defoliation of plants, processes for preparing these compositions and methods for the desiccation and/or defoliation of plants using the compounds I or II have been found.

The organic molecular moieties mentioned for the substituents $R^1$ to $R^9$ or as radicals on phenyl rings or heterocycles are, like the meaning halogen, collective terms for individual lists of the separate group members. All hydrocarbon chains, ie. all alkyl, haloalkyl, alkenyl, alkynyl, hydroxyalkyl, cyanoalkyl, alkoxy, alkylthio, alkylcarbonyl, haloalkylcarbonyl, alkoxycarbonyl, alkoxycarbonylalkyl, alkylcarbonyloxy, alkylcarbonylalkyl, alkylcarbonyloxyalkyl, phenylalkyl, alkoxyalkyl and alkylthioalkyl moieties can be straight-chain or branched. Halogenated substituents preferably carry one to five identical or different halogen atoms.

Specific examples are:

halogen is: fluorine, chlorine, bromine and iodine, preferably fluorine and chlorine;

$C_1$–$C_6$-alkyl and the alkyl moieties of $C_1$–$C_6$-alkoxy-$C_1$–$C_6$-alkyl, $C_1$–$C_6$-alkylthio-$C_1$–$C_6$-alkyl, ($C_1$–$C_6$-alkyl)carbonyl-$C_1$–$C_6$-alkyl, ($C_1$–$C_6$-alkoxy)carbonyl-$C_1$–$C_6$-alkyl, ($C_1$–$C_6$-alkyl)carbonyloxy-$C_1$–$C_6$-alkyl and phenyl-$C_1$–$C_6$-alkyl are: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_1$–$C_4$-alkyl, in particular methyl and ethyl;

$C_1$–$C_6$-haloalkyl is: $C_1$–$C_6$-alkyl as mentioned above, which is partially or completely substituted by fluorine, chlorine and/or bromine, eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-fluoropropyl, 3-chloropropyl and heptafluoropropyl, preferably $C_1$–$C_4$-haloalkyl, in particular trifluoromethyl and 1,2-dichloroethyl;

$C_3$–$C_6$-alkenyl is: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, and preferably $C_3$- or $C_4$-alkenyl;

$C_3$–$C_6$-alkynyl is: prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-in-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably $C_3$- or $C_4$-alkynyl, in particular prop-2-yn-3-yl;

hydroxy-$C_1$–$C_6$-alkyl eg. is: hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-2-yl, 3-hydroxybut-2-yl, 4-hydroxybut-1-yl, 2-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl and 2-hydroxymethylprop-2-yl, preferably hydroxy-$C_1$–$C_6$-alkyl, in particular 2-hydroxyeth-1-yl;

cyano-$C_1$–$C_6$-alkyl eg. is: cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl, preferably cyano-$C_1$–$C_4$-alkyl, in particular 2-cyanoeth-1-yl;

phenyl-$C_1$–$C_6$-alkyl eg. is: benzyl, 1-phenyleth-1-yl, 2-phenyleth-1-yl, 1-phenylprop-1-yl, 2-phenylprop-1-yl, 3-phenylprop-1-yl, 1-phenylprop-2-yl, 2-phenylprop-2-yl, 1-phenylbut-1-yl, 2-phenylbut-1-yl, 3-phenylbut-1-yl, 4-phenylbut-1-yl, 1-phenylbut-2-yl, 2-phenylbut-2-yl, 1-phenylbut-3-yl, 2-phenylbut-3-yl, 1-phenyl-2-methylprop-3-yl, 2-phenyl-2-methylprop-3-yl, 3-phenyl-2-methylprop-3-yl and 2-benzylprop-2-yl, preferably phenyl-$C_1$–$C_4$-alkyl, in particular 2-phenyleth-1-yl;

$C_1$–$C_6$-alkoxy and the alkoxy moiety of $C_1$–$C_6$-alkoxy-$C_1$–$C_6$-alkyl are: methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably $C_1$–$C_4$-alkoxy, in particular methoxy, ethoxy and 1-methylethoxy;

$C_1$–$C_6$-alkylthio is: methylthio, ethylthio, n-propylthio, 1-methylethylthio, n-butylthio, 1-methylpropylthio, 2-methylpropylthio, 1,11-dimethylethylthio, n-pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, n-hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, preferably $C_1$–$C_4$-alkylthio, in particular methylthio, ethylthio and 1-methylethylthio;

($C_1$–$C_6$-alkyl)carbonyl and the alkylcarbonyl moiety of ($C_1$–$C_6$-alkyl)carbonyl-$C_1$–$C_6$-alkyl are: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, n-hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably ($C_1$–$C_4$-alkyl)carbonyl, in particular methylcarbonyl and ethylcarbonyl;

($C_1$–$C_6$-haloalkyl)carbonyl is: ($C_1$–$C_6$-alkyl)carbonyl as mentioned above, which is partially or completely substituted by fluorine, chlorine and/or bromine, eg. chloromethylcarbonyl, dichloromethylcarbonyl, trichloromethylcarbonyl, fluoromethylcarbonyl, difluoromethylcarbonyl, trifluoromethylcarbonyl, chlorofluoromethylcarbonyl, dichlorofluoromethylcarbonyl, chlorodifluoromethylcarbonyl, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 3-chloropropylcarbonyl, heptafluoropropylcarbonyl, preferably ($C_1$–$C_4$-haloalkyl)carbonyl, in particular trifluoromethylcarbonyl, chloromethylcarbonyl, dichloromethylcarbonyl and trichloromethylcarbonyl;

($C_1$–$C_6$-alkoxy)carbonyl and the alkoxycarbonyl moiety of ($C_1$–$C_6$-alkoxy)carbonyl-$C_1$–$C_6$-alkyl are: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl and 1-ethyl-2-methylpropoxycarbonyl, preferably ($C_1$–$C_4$-alkoxy)carbonyl, in particular methoxycarbonyl, ethoxycarbonyl and 1-methylethoxycarbonyl;

the alkylcarbonyloxy moiety of ($C_1$–$C_6$-alkyl)carbonyloxy-$C_1$–$C_6$-alkyl is: methylcarbonyloxy, ethylcarbonyloxy, n-propylcarbonyloxy, (1-methylethyl)carbonyloxy, n-butylcarbonyloxy, (1-methylpropyl)carbonyloxy, (2-methylpropyl)carbonyloxy, (1,1-dimethylethyl)carbonyloxy, n-pentylcarbonyloxy, (1-methylbutyl)carbonyloxy, (2-methylbutyl)carbonyloxy, (3-methylbutyl)carbonyloxy, (2,2-dimethylpropyl)carbonyloxy, (1-ethylpropyl)carbonyloxy, n-hexylcarbonyloxy, (1,1-dimethylpropyl)carbonyloxy, (1,2-dimethylpropyl)carbonyloxy, (1-methylpentyl)carbonyloxy, (2-methylpentyl)carbonyloxy, (3-methylpentyl)carbonyloxy, (4-methylpentyl)carbonyloxy, (1,1-dimethylbutyl)carbonyloxy, (1,2-dimethylbutyl)carbonyloxy, (1,3-dimethylbutyl)carbonyloxy, (2,2-dimethylbutyl)carbonyloxy, (2,3-dimethylbutyl)carbonyloxy, (3,3-dimethylbutyl)carbonyloxy, (1-ethylbutyl)-carbonyloxy, (2-ethylbutyl)
carbonyloxy, (1,1,2-trimethylpropyl)carbonyloxy, (1,2,
2-trimethylpropyl)carbonyloxy, (1-ethyl-1-
methylpropyl)carbonyloxy and (1-ethyl-2-
methylpropyl)carbonyloxy, preferably ($C_1$–$C_4$-alkyl)
carbonyloxy, in particular methylcarbonyloxy and
ethylcarbonyloxy;

$C_3$–$C_6$-cycloalkyl is: cyclopropyl, cyclobutyl, cyclopentyl and cyclohexyl, preferably cyclopropyl and cyclopentyl;

3- to 7-membered azaheterocycles which, in addition to carbon ring members, can also contain an oxygen or sulfur atom as a ring member, eg. pyrrolidin-1-yl, isoxazolidin-2-yl, isothiazolidin-2-yl, oxazolidin-3-yl, thiazolidin-3-yl, piperidin-1-yl, azepin-1-yl, morpholin-1-yl and thiomorpholin-1-yl.

All phenyl rings are preferably unsubstituted or carry a halogen, methyl, trifluoromethyl or methoxy substituent.

Depending on the particular substituents, the compounds I and II can be present in the form of their agriculturally utilizable salts, the nature of the salt in general not mattering. Customarily, salts of those bases or those acids are suitable which do not adversely affect the herbicidal action of I or II.

Suitable basic salts are particularly those of the alkali metals, preferably the sodium and potassium salts, those of the alkaline earth metals, preferably calcium, magnesium and barium salts, and those of the transition metals, preferably manganese, copper, zinc and iron salts, as well as ammonium salts in which the ammonium ion can, if desired, carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, and in addition phosphonium salts, sulfonium salts such as, preferably, tri-($C_1$–$C_4$-alkyl)sulfonium salts, and sulfoxonium salts such as, preferably, tri-($C_1$–$C_4$-alkyl)sulfoxonium salts.

Acid addition salts are, for example, the hydrochlorides and bromides, sulfates, nitrates, phosphates, oxalates or the dodecylbenzenesulfonates of compounds I.

In relation to the use of the substituted cinnamic oxime derivatives I and the substituted cinnamic hydroxamide derivatives II as herbicides, those compounds are preferred in which the variables have the following meanings, namely in each case per se or in combination:

$R^1$ is halogen or cyano, in particular chlorine, bromine or cyano;

$R^2$ is hydrogen, fluorine or chlorine;

$R^3$ is hydrogen or halogen;

$R^4$ is hydrogen, halogen or $C_1$–$C_4$-alkyl;

Y is oxygen or a chemical bond;

Y' is oxygen;

$R^5$ is $C_1$–$C_4$-alkyl, $C_1$–$C_6$-alkoxy-$C_1$–$C_6$-alkyl, ($C_1$–$C_6$-alkoxy)carbonyl-$C_1$–$C_6$-alkyl or, if Y is a chemical bond, is hydrogen;

$R^5$, is hydrogen or $C_1$–$C_4$-alkyl;

$R^6$ is hydrogen, $C_1$–$C_4$-alkyl or $C_3$–$C_4$-alkenyl;

Cyc is a radical

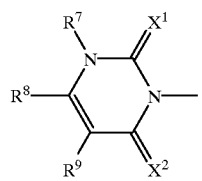

$X^1$ and $X^2$ independently of one another being oxygen or sulfur;

$R^7$ being methyl or amino and $R^8$ being $C_1$–$C_4$-haloalkyl, in particular trifluoromethyl or chlorodifluoromethyl and $R^9$ being hydrogen.

Particularly preferred substituted cinnamic oxime derivatives I are those of the following Tables 1 and 2:

TABLE 1

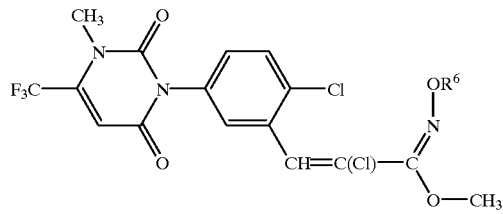

I{$R^2$, $R^3$ = H;
$R^1$, $R^4$ = Cl; $R^5$ = $CH_3$;
Y = O; Cyc =
1-$CH_3$-6-$CF_3$-
uracil-3-yl}

| No. | $R^6$ |
|---|---|
| 1.01 | H |
| 1.02 | $CH_3$ |
| 1.03 | $C_2H_5$ |
| 1.04 | n-$C_3H_7$ |
| 1.05 | i-$C_3H_7$ |
| 1.06 | n-$C_4H_9$ |
| 1.07 | n-$C_5H_{11}$ |
| 1.08 | $(CH_2)_2$—$OCH_3$ |
| 1.09 | $(CH_2)_2$—$OC_2H_5$ |
| 1.10 | $CH_2$—$CH(CH_3)$—$OCH_3$ |
| 1.11 | $(CH_2)_2$—$CH_2F$ |
| 1.12 | $CH_2$—$CF_3$ |
| 1.13 | $CH_2$—$CCl_3$ |
| 1.14 | Cyclopropyl |
| 1.15 | Cyclopentyl |
| 1.16 | Cyclohexyl |
| 1.17 | $CH_2CH$=$CH_2$ |
| 1.18 | $CH_2C$≡$CH$ |
| 1.19 | $CH_2$—$CH_2OH$ |
| 1.20 | $CH_2$—$CH(CH_3)OH$ |
| 1.21 | $(CH_2)_2$—$SCH_3$ |
| 1.22 | $(CH_2)_3$—$SCH_3$ |
| 1.23 | $CH_2CN$ |
| 1.24 | $(CH_2)_2$—$CH_2CN$ |
| 1.25 | $CH_2$—CO—$OCH_3$ |
| 1.26 | $CH_2$—CO—$OC_2H_5$ |
| 1.27 | $CH(CH_3)$—CO—$OCH_3$ |
| 1.28 | $CH(CH_3)$—CO—$OC_2H_5$ |
| 1.29 | $CH_2$—CO—$CH_3$ |
| 1.30 | $CH_2$—CO—$C_2H_5$ |
| 1.31 | $CH_2O$—CO—$CH_3$ |
| 1.32 | $CH_2O$—CO—$C_2H_5$ |
| 1.33 | $CH_2$-phenyl |
| 1.34 | $CH_2$—(4-Cl-phenyl) |
| 1.35 | $CH_2$-(4-$CF_3$-phenyl) |

TABLE 1-continued

I{$R^2$, $R^3$ = H; $R^1$, $R^4$ = Cl; $R^5$ = $CH_3$; Y = O; Cyc = 1-$CH_3$-6-$CF_3$-uracil-3-yl}

| No. | $R^6$ |
|---|---|
| 1.36 | $CH_2$-(3-$NO_2$-phenyl) |

TABLE 2

I{$R^2$, $R^3$ = H; $R^1$, $R^4$ = Cl; $R^6$ = $CH_3$; Y = O; Cyc = 1-$CH_3$-6-$CF_3$-uracil-3-yl}

| No. | $R^5$ |
|---|---|
| 2.01 | $CH_3$ |
| 2.02 | $C_2H_5$ |
| 2.03 | n-$C_3H_7$ |
| 2.04 | i-$C_3H_7$ |
| 2.05 | n-$C_4H_9$ |
| 2.06 | n-$C_5H_{11}$ |
| 2.07 | $(CH_2)_2$—$OCH_3$ |
| 2.08 | $(CH_2)_2$—$OC_2H_5$ |
| 2.09 | $CH_3CH(CH_3)$—$OCH_3$ |
| 2.10 | $(CH_2)_2$—$CH_2F$ |
| 2.11 | $CH_2$—$CF_3$ |
| 2.12 | $CH_2$—$CCl_3$ |
| 2.13 | Cyclopropyl |
| 2.14 | Cyclopentyl |
| 2.15 | Cyclohexyl |
| 2.16 | $CH_2CH$=$CH_2$ |
| 2.17 | $CH_2C$≡$CH$ |
| 2.18 | $CH_2$—$CH_2OH$ |
| 2.19 | $CH_2$—$CH(CH_3)OH$ |
| 2.20 | $(CH_2)_2$—$SCH_3$ |
| 2.21 | $(CH_2)_3$—$SCH_3$ |
| 2.22 | $CH_2CN$ |
| 2.23 | $(CH_2)_2$—$CH_2CN$ |
| 2.24 | $CH_2$—CO—$OCH_3$ |
| 2.25 | $CH_2$—CO—$OC_2H_5$ |
| 2.26 | $CH(CH_3)$—CO—$OCH_3$ |
| 2.27 | $CH(CH_3)$—CO—$OC_2H_5$ |
| 2.28 | $CH_2$—CO—$CH_3$ |
| 2.29 | $CH_2$—CO—$C_2H_5$ |
| 2.30 | $CH_2$—O—CO—$CH_3$ |
| 2.31 | $CH_2$—O—CO—$C_2H_5$ |
| 2.32 | $CH_2$-phenyl |
| 2.33 | $CH_2$-(4-Cl-phenyl) |
| 2.34 | $CH_2$-(4-$CF_3$-phenyl) |
| 2.35 | $CH_2$-(3-$NO_2$-phenyl) |
| 2.36 | phenyl |
| 2.37 | 4-Cl-phenyl |
| 2.38 | 4-F-phenyl |
| 2.39 | (4-$OCH_3$-phenyl) |
| 2.40 | (3-$NO_2$-phenyl) |
| 2.41 | (4-Cl-,3-$COOCH_3$-phenyl) |

In addition, the following substituted cinnamic oxime derivatives I are particularly preferred:

the compounds 3.01–3.36, which differ from the compounds 1.01–1.36 in that $R^2$ is fluorine;

the compounds 4.01–4.36, which differ from the compounds 1.01–1.36 in that $R^4$ is bromine;

the compounds 5.01–5.36, which differ from the compounds 1.01–1.36 in that $R^4$ is methyl;

the compounds 6.01–6.36, which differ from the compounds 1.01–1.36 in that $R^4$ is hydrogen;

the compounds 7.01–7.36, which differ from the compounds 1.01–1.36 in that $R^2$ is fluorine and $R^4$ is bromine;

the compounds 8.01–8.36, which differ from the compounds 1.01–1.36 in that $R^2$ is fluorine and $R^4$ is methyl;

the compounds 9.01–9.36, which differ from the compounds 1.01–1.36 in that $R^2$ is fluorine and $R^4$ is hydrogen;

the compounds 10.01–10.36, which differ from the compounds 1.01–1.36 in that $R^2$ is fluorine and Y is sulfur;

the compounds 11.01–11.36, which differ from the compounds 1.01–1.36 in that $R^4$ is bromine and Y is sulfur;

the compounds 12.01–12.36, which differ from the compounds 1.01–1.36 in that $R^4$ is methyl and Y is sulfur;

the compounds 13.01–13.36, which differ from the compounds 1.01–1.36 in that $R^4$ is hydrogen and Y is sulfur;

the compounds 14.01–14.36, which differ from the compounds 1.01–1.36 in that $R^2$ is fluorine, $R^4$ is bromine and Y is sulfur;

the compounds 15.01–15.36, which differ from the compounds 1.01–1.36 in that $R^2$ is fluorine, $R^4$ is methyl and Y is sulfur;

the compounds 16.01–16.36, which differ from the compounds 1.01–1.36 in that $R^2$ is fluorine, $R^4$ is hydrogen and Y is a chemical bond;

the compounds 17.01–17.36, which differ from the compounds 1.01–1.36 in that $R^2$ is fluorine and Y is a chemical bond;

the compounds 18.01–18.36, which differ from the compounds 1.01–1.36 in that $R^4$ is bromine and Y is a chemical bond;

the compounds 19.01–19.36, which differ from the compounds 1.01–1.36 in that $R^4$ is methyl and Y is a chemical bond;

the compounds 20.01–20.36, which differ from the compounds 1.01–1.36 in that $R^4$ is hydrogen and Y is a chemical bond;

the compounds 21.01–21.36, which differ from the compounds 1.01–1.36 in that $R^2$ is fluorine, $R^4$ is bromine and Y is a chemical bond;

the compounds 22.01–22.36, which differ from the compounds 1.01–1.36 in that $R^2$ is fluorine, $R^4$ is methyl and Y is a chemical bond;

the compounds 23.01–23.36, which differ from the compounds 1.01–1.36 in that $R^2$ is fluorine, $R^4$ is hydrogen and Y is a chemical bond;

the compounds 24.01–24.41, which differ from the compounds 2.01–2.41 in that $R^2$ is fluorine;

the compounds 25.01–25.41, which differ from the compounds 2.01–2.41 in that $R^2$ is bromine;

the compounds 26.01–26.41, which differ from the compounds 2.01–2.41 in that $R^2$ is methyl;

the compounds 27.01–27.41, which differ from the compounds 2.01–2.41 in that $R^2$ is hydrogen;

the compounds 28.01–28.41, which differ from the compounds 2.01–2.41 in that $R^4$ is bromine and $R^2$ is fluorine;

the compounds 29.01–29.41, which differ from the compounds 2.01–2.41 in that $R^4$ is methyl and $R^2$ is fluorine;

the compounds 30.01–30.41, which differ from the compounds 2.01–2.41 in that $R^4$ is hydrogen and $R^2$ is fluorine;

the compounds 31.01–31.41, which differ from the compounds 2.01–2.41 in that $R^2$ is fluorine and Y is sulfur;

the compounds 32.01–32.41, which differ from the compounds 2.01–2.41 in that $R^4$ is bromine and Y is sulfur;

the compounds 33.01–33.41, which differ from the compounds 2.01–2.41 in that $R^4$ is methyl and Y is sulfur;

the compounds 34.01–34.41, which differ from the compounds 2.01–2.41 in that $R^4$ is hydrogen and Y is sulfur;

the compounds 35.01–35.41, which differ from the compounds 2.01–2.41 in that $R^2$ is fluorine, $R^4$ is bromine and Y is sulfur;

the compounds 36.01–36.41, which differ from the compounds 2.01–2.41 in that $R^2$ is fluorine, $R^4$ is methyl and Y is sulfur;

the compounds 37.01–37.41, which differ from the compounds 2.01–2.41 in that $R^2$ is fluorine, $R^4$ is hydrogen and Y is sulfur;

the compounds 38.01–38.41, which differ from the compounds 2.01–2.41 in that $R^2$ is fluorine and Y is a chemical bond;

the compounds 39.01–39.41, which differ from the compounds 2.01–2.41 in that $R^2$ is bromine and Y is a chemical bond;

the compounds 40.01–40.41, which differ from the compounds 2.01–2.41 in that $R^4$ is methyl and Y is a chemical bond;

the compounds 41.01–41.41, which differ from the compounds 2.01–2.41 in that $R^4$ is hydrogen and Y is a chemical bond;

the compounds 42.01–42.41, which differ from the compounds 2.01–2.41 in that $R^2$ is fluorine, $R^4$ is bromine and Y is a chemical bond;

the compounds 43.01–43.41, which differ from the compounds 2.01–2.41 in that $R^2$ is fluorine, $R^4$ is methyl and Y is a chemical bond;

the compounds 44.01–44.41, which differ from the compounds 2.01–2.41 in that $R^2$ is fluorine, $R^4$ is hydrogen and Y is a chemical bond;

the compounds 45.01–45.36, which differ from the compounds 1.01–1.36 in that $R^2$ is fluorine and Cyc is 1-$NH_2$-6-$CF_3$-uracil-3-yl;

the compounds 46.01–46.36, which differ from the compounds 1.01–1.36 in that $R^4$ is bromine and Cyc is 1-$NH_2$-6-$CF_3$-uracil-3-yl;

the compounds 47.01–47.36, which differ from the compounds 1.01–1.36 in that $R^4$ is methyl and Cyc is 1-$NH_2$-6-$CF_3$-uracil-3-yl;

the compounds 48.01–48.36, which differ from the compounds 1.01–1.36 in that $R^4$ is hydrogen and Cyc is 1-$NH_2$-6-$CF_3$-uracil-3-yl;

the compounds 49.01–49.36, which differ from the compounds 1.01–1.36 in that $R^2$ is fluorine, $R^4$ is bromine and Cyc is 1-$NH_2$-6-$CF_3$-uracil-3-yl;

the compounds 50.01–50.36, which differ from the compounds 1.01–1.36 in that $R^2$ is fluorine, $R^4$ is methyl and Cyc is 1-$NH_2$-6-$CF_3$-uracil-3-yl;

the compounds 51.01–51.36, which differ from the compounds 1.01–1.36 in that $R^2$ is fluorine, $R^4$ is hydrogen and Cyc is 1-$NH_2$-6-$CF_3$-uracil-3-yl.

The substituted cinnamic oxime derivatives of the formula I and the substituted cinnamic hydroxamide derivatives of the formula II are obtainable in various ways, preferably by one of the following processes:

a) Alkylation of a subst. cinnamic hydroxamide derivative of the formula II where $R^{5'}$=hydrogen or of the formula IV:

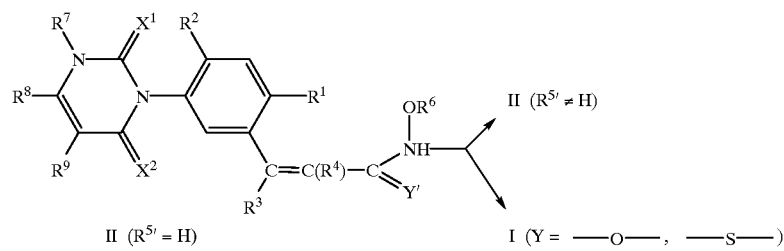

-continued

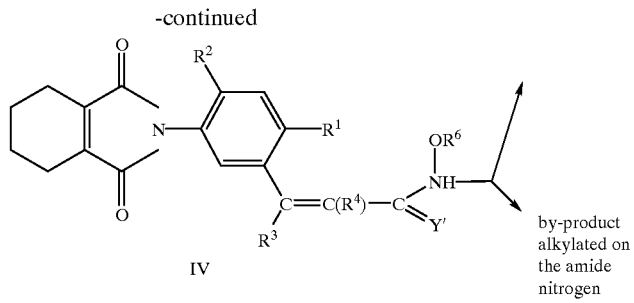

by-product alkylated on the amide nitrogen

As a rule, the reaction is carried out in an inert solvent or diluent, preferably in the presence of a base.

Suitable solvents are, for example, protic solvents such as the lower alcohols, preferably ethanol, if desired in a mixture with water, or aprotic solvents such as aliphatic or cyclic ethers, preferably 1,2-dimethoxyethane, tetrahydrofuran and dioxane, aliphatic ketones, preferably acetone, amides, preferably dimethylformamide, sulfoxides, preferably dimethyl sulfoxide, ureas such as tetramethylurea and 1,3-dimethyltetrahydro-2(1H)-pyrimidinone (DMPU), carboxylic acid esters such as ethyl acetate, or halogenated aliphatic or aromatic hydrocarbons such as dichloromethane and chlorobenzene.

Alkylation is usually carried out using the halide, preferably the chloride or bromide, the sulfate, a sulfonate, preferably a methanesulfonate (mesylate) such as trifluoromethanesulfonate (triflate) or a benzenesulfonate such as p-toluenesulfonate (tosylate) and p-bromobenzenesulfonate (brosylate), or using a diazo compound, eg. diazomethane.

Suitable bases are inorganic bases, eg. carbonates such as potassium carbonate and sodium carbonate, hydrogencarbonates such as potassium and sodium hydrogencarbonate, alkali metal hydrides such as sodium hydride and potassum hydride, and also organic bases, eg. amines such as triethylamine, pyridine and N,N-diethylaniline, or alkali metal alkoxides such as sodium methoxide, sodium ethoxide and potassium t-butoxide.

Preferably, 0.5 to 2 times the molar amount both of base and of alkylating agent is used, based on the amount of II ($R^{5'}$=H) or IV.

In general, a reaction temperature from −78° C. up to the boiling point of the reaction mixture is recommended, in particular from −60 to 60° C.

Customarily, the corresponding, amide nitrogen-substituted cinnamic hydroxamide derivatives (II) are also formed in the alkylation of the compounds of the formula II (where $R^5$=hydrogen) or IV in addition to the substituted cinnamic oxime derivatives I in which Y is oxygen or sulfur. The ratio in which the two products are formed depends on the reaction temperature, on the alkylating agent, the base used and also on the respective starting compound II (where $R^5$=hydrogen) or IV. According to present knowledge, the compound I is usually formed in excess. It can normally be separated from the by-products in a manner known per se, eg. by crystallization or chromatography.

b) Alkylation of the substituted cinnamic oxime derivative I where $R^6$=hydrogen in the presence of a base:

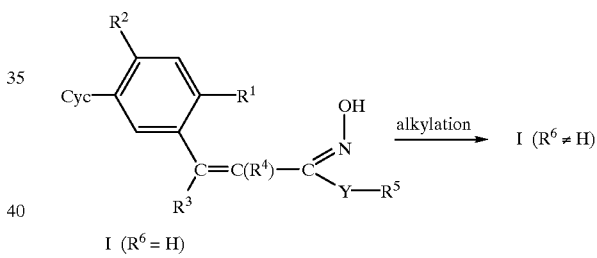

Reference may be made to the details under method a) in respect of the reaction conditions.

Acylation or sulfonylation of a cinnamic hydroxamide derivative of the formula II where $R^{5'}$=hydrogen or of the formula IV:

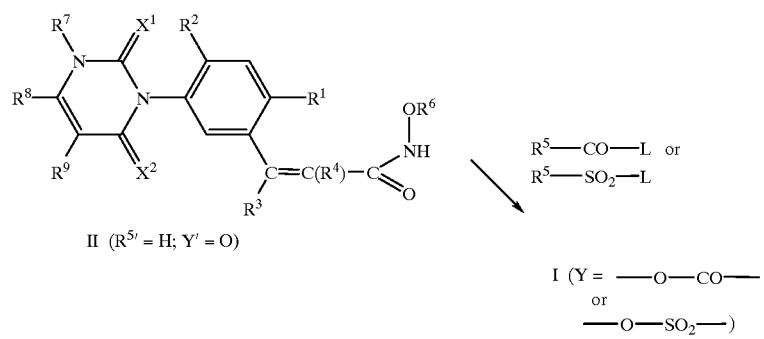

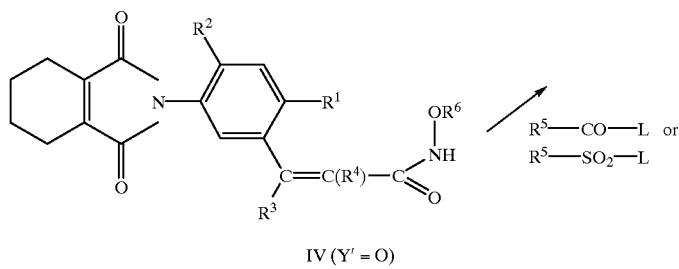

IV (Y' = O)

L is a customary leaving group such as halogen, alkylcarbonyloxy, haloalkylcarbonyloxy or imidazolyl.

The reaction is normally performed in an inert solvent or diluent, eg. the solvents mentioned for the alkylation under a) or mixtures thereof being suitable.

The acylating agent can also be prepared in situ from the corresponding carboxylic acid, the reaction then preferably being carried out in the presence of a customary condensation aid. Suitable condensation aids are eg. oxalyl chloride, carbonyldiimidazole, carbodiimides such as dicyclohexylcarbodiimide, halogenating agents such as thionyl chloride, phosphorus oxychloride, phosgene, phosphorus trichloride and phosphorus pentachloride, or methyl or ethyl chloroformate.

Expediently, approximately stoichiometric amounts of acylating agent and cinnamic hydroxamide derivative II (where $R^{5'}$=hydrogen) or IV are used, or eg. to optimize the conversion of II or IV, an excess of acylating agent up to approximately 10 mol %.

Depending on the starting substances, it may be advantageous to work in the presence of a base. Suitable bases for this purpose are inorganic bases, eg. carbonates such as sodium and potassium carbonate, alkali metal hydrogencarbonates such as sodium and potassium hydrogencarbonate, alkali metal hydrides such as sodium and potassium hydride, and also organic bases, eg. amines such as triethylamine, pyridine and N,N-diethylaniline, or alkali metal alkoxides such as sodium methoxide, sodium ethoxide and potassium tert-butoxide.

Even a catalytic amount of base of eg. 0.01 mol equivalents, based on II or IV, can positively affect the course of the reaction. On the other hand, an amount of base of above 200 mol % normally provides no additional advantages. The reaction can generally be carried out at from –20° C. up to the boiling point of the reaction mixture. It is preferably carried out at from 0 to 80° C.

d) Reaction of a hydroximino halide of the formula Ia with an alcohol or mercaptan derivative:

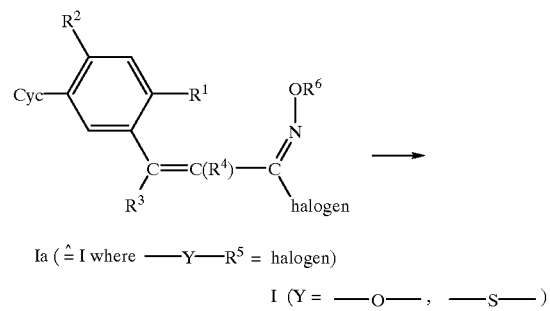

Ia ($\hat{=}$ I where —Y—$R^5$ = halogen)

I (Y = —O—, —S—)

Advantageously, the alcohol or mercaptan derivatives used are the alcohols $R^5$—OH or mercaptans $R^5$—SH and their salts, in particular those of the alkali or alkaline earth metals.

Suitable solvents or diluents are eg. aliphatic or cyclic ethers such as diethyl ether and tetrahydrofuran, aliphatic ketones such as acetone, hydrocarbons such as n-pentane, cyclohexane and petroleum ether, aromatic hydrocarbons such as benzene and toluene, halogenated aliphatic or aromatic hydrocarbons such as dichloromethane and chlorobenzene, esters such as ethyl acetate, amides such as dimethylformamide and N-methylpyrrolidone, sulfoxides such as dimethyl sulfoxide, as well as mixtures of these solvents. The alcohol and mercaptan derivatives themselves are also suitable as solvents or diluents.

The quantity ratio of Ia to alcohol or mercaptan derivative is not critical. Customarily, approximately equimolar amounts are employed. However, it may also be expedient to employ the alcohol or mercaptan derivative in an excess such that it simultaneously serves as a solvent or diluent.

In general, a reaction temperature from –78° C. up to the reflux temperature of the solvents used is recommended, in particular from 0 to 80° C.

When reacting Ia with an alcohol $R^5$—OH or mercaptan $R^5$—SH, the process is particularly advantageously carried out in the presence of a base, both inorganic bases, eg. carbonates, hydrogencarbonates or alkali metal hydrides, and organic bases, eg. amines such as triethylamine, pyridine and N,N-dimethylaniline, or alkali metal alkoxides being suitable. An alkoxide of the alcohol $R^5$-OH is expediently used.

The base can be employed in catalytic, sub-stoichiometric or stoichiometric amounts or in an excess, up to 5 times the molar amount, based on I.

e) Halogenation of compounds of the formula II where Y'=oxygen and $R^{5'}$=hydrogen or the formula IV where Y' oxygen:

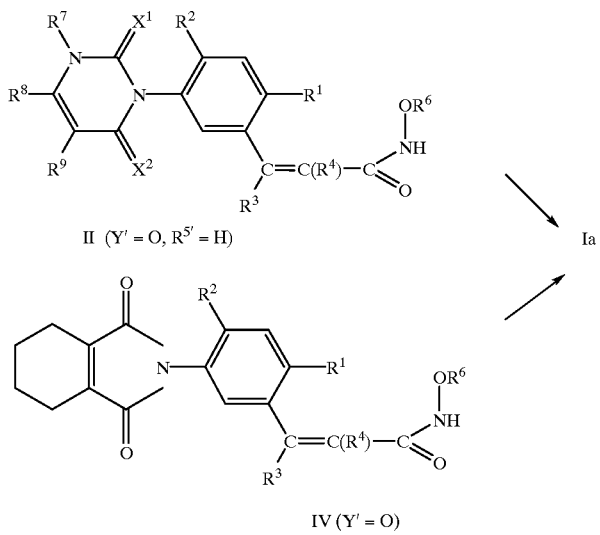

II (Y' = O, R⁵' = H)

IV (Y' = O)

Customarily, the process is carried out in an inert solvent or diluent, aprotic organic liquids, for example aliphatic or aromatic hydrocarbons such as n-hexane, benzene, toluene and o-, m- or p-xylene, halogenated aliphatic hydrocarbons such as methylene chloride, chloroform and 1,2-dichloroethane, halogenated aromatic hydrocarbons such as chlorobenzene, tertiary amines such as N,N-dimethylaniline or nitriles such as acetonitrile in particular being suitable.

Suitable halogenating agents are especially thionyl chloride, phosphorus tetrachloride, phosphorus oxychloride, phosphorus pentabromide or phosphorus oxybromide. The use of a mixture of phosphorus pentachloride and phosphorus oxychloride or of phosphorus pentabromide and phosphorus oxybromide can also be particularly advantageous, it then being possible to carry out the reaction without diluents in an excess of phosphorus oxychloride or phosphorus oxybromide.

When using thionyl chloride as a halogenating agent, it is recommended to add a catalytic amount of dimethylformamide. A mixture of a tetrahalomethane such as carbon tetrachloride and carbon tetrabromide, and an unsubstituted or substituted triphenylphosphane, eg. triphenylphosphane or tri-(o-tolyl)-phosphane, has proven particularly suitable.

At least equimolar amounts of halogenating agent and starting compound II (Y'=O, R⁵'=H) or IV (Y'=O) are needed for a complete reaction. In general, an excess of halogenating agent, up to approximately 8 times the molar amount, based on II or IV, has a favorable effect on the course of the reaction.

The reaction temperature is in general from 0 C to the reflux temperature of the reaction mixture, preferably from 20 to 120° C.

Conversion of a cinnamonitrile V to a compound of the formula

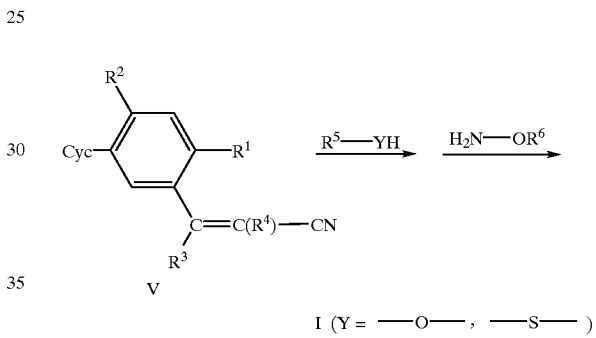

I (Y = —O—, —S—)

The reaction is customarily carried out in two stages, by first reacting the cinnamonitrile V with an alcohol or mercaptan R⁵—YH and reacting the imidoester or thioimidoester VI obtained in this way, if desired without isolation from the reaction mixture, with a hydroxylamine H₂N—OR⁶.

The reaction of V with R⁵—YH can be carried out in an inert solvent or diluent or without solvent in an excess of the alcohol or mercaptan. Often an acidic or Lewis acid catalyst is beneficial, preferably in approximately catalytic amount or in an amount of up to approximately 200 mol %, based on the amount of V.

Suitable inert solvents or diluents are particularly organic solvents, eg. aliphatic or cyclic ethers such as diethyl ether, tetrahydrofuran and dimethoxyethane, aliphatic, cyclic or aromatic hydrocarbons such as n-pentane, petroleum ether, cyclohexane, toluene and the xylenes, amides such as dimethylformamide and N-methylpyrrolidone, halogenated hydrocarbons such as dichloromethane, chlorobenzene and 1,2-dichloromethane, or mixtures of said solvents.

Suitable acidic catalysts are inorganic, preferably anhydrous acids, eg. hydrogen chloride, hydrogen bromide, nitric acid, sulfuric acid, also oleum, or perchloric acid, as well as organic acids such as acetic acid, propionic acid, p-toluenesulfonic acid or trifluoroacetic acid. Examples of Lewis acid catalysts are titanium tetrachloride, tin(II) chloride, iron(III) chloride, aluminum trichloride, ethylaluminum trichloride, titanium tetraisopropoxide and boron trifluoride etherate.

The amount of alcohol or mercaptan is not critical. Normally, from 1 to 10 mol of alcohol or mercaptan per mole of V are adequate for an optimum reaction of V. If the reaction is carried out without solvent in the alcohol concerned, this can also be present in a relatively large excess.

If the imidoester or thioimidoester VI is obtained in the first stage as a salt, it is recommended to liberate the neutral compound before the reaction with the hydroxylamine $H_2N-OR^6$ is performed.

Hydroxylamines which are obtainable in the form of their salts, in particular as hydrochlorides, hydrobromides or sulfates, or are obtained during preparation as salts can be liberated before reaction thereof by addition of a suitable base, suitable bases in particular being those mentioned in method a).

The reaction of the resulting imidoester or thioimidoester VI with $H_2N-OR^6$ is in general carried out in an inert solvent or diluent. For this purpose, those suitable in addition to the abovementioned solvents are additionally alcohols such as methanol, ethanol and isopropanol, nitriles such as acetonitrile, amines such as triethylamine, pyridine and N,N-dimethylaniline, or even water.

(Thio)imidoesters VI and hydroxylamine are expediently reacted with one another in approximately equimolar amounts. In order to react the (thio)imidoester VI as completely as possible, however, it may be advisable to employ the hydroxylamine $H_2N-OR^6$ in an excess, up to approximately 10 mol %.

The reaction temperature for both stages is in general from −20 to 120° C., in particular from 0° C. up to the boiling point of the reaction mixture.

g) Oximation of a cinnamaldehyde or cinnamic ketone of the formula VII:

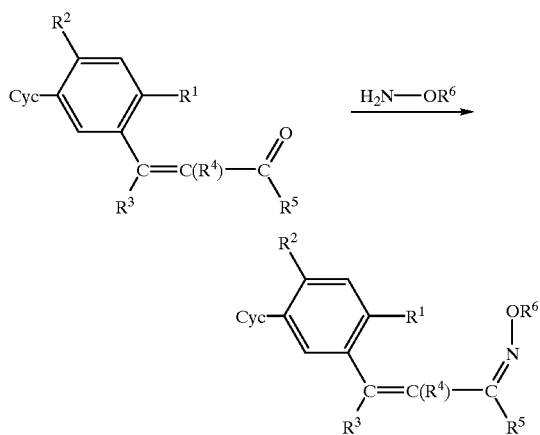

The reaction of VII with a hydroxylamine $H_2N-OR_6$ is normally carried out in an inert organic solvent or diluent, eg. in an aromatic hydrocarbon such as toluene or the xylenes, in a chlorinated hydrocarbon such as dichloromethane, chloroform or chlorobenzene, in an ether such as diethyl ether, 1,2-dimethoxyethane or tetrahydrofuran, in an alcohol such as methanol or ethanol, in water or in a mixture of said solvents.

If the hydroxylamines $H_2N-OR^6$ are present as salts, eg. as hydrochlorides or oxalates, liberation thereof by means of base such as, preferably, sodium carbonate, potassium carbonate, sodium hydrogencarbonate, triethylamine and pyridine, is advisable.

The amount of hydroxylamine is preferably from 80 to 800 mol %, in particular from 100 to 300 mol %, based on the amount of VII.

The resulting water of reaction can be removed from the reaction mixture, if desired, by distillation or with the aid of a water separator.

Customarily, the reaction temperature is from −30 to 150° C., preferably from 0 to 130° C.

h) Conversion of a cinnamic oxime of the formula VIII

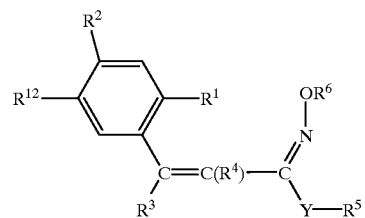

$R^{12}$ being nitro, amino, isocyanato, isothiocyanato, ($C_1$–$C_6$-alkyl)carbamato or phenylcarbamato
to the substituted cinnamic oxime derivatives I according to a process described in WO 93/06090.

The compounds of the formula VIII are novel. They are obtainable in turn according to one of the processes described above for preparing compounds I. Further methods for preparing the compounds VIII can also be taken from WO 93/06090.

The compounds of the formula V are known or can be prepared in a manner known per se (cf. eg. WO 93/06090).

The cinnamic hydroxamide derivatives of the formulae II and IV (where Y'=oxygen) are accessible eg. from cinnamic acids of the formulae IX and X:

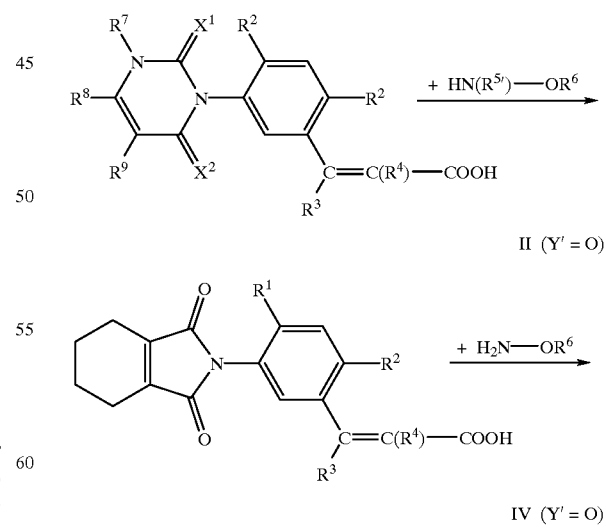

The reaction is customarily performed in an inert solvent or diluent in the presence of a condensation aid or without solvent in an excess of the condensation aid.

Suitable solvents or diluents are, in particular, organic solvents, eg. aliphatic or cyclic ethers, such as diethyl ether, tetrahydrofuran and dimethoxyethane, aliphatic, cyclic or aromatic hydrocarbons such as n-pentane, petroleum ether, cyclohexane, toluene and the xylenes, alcohols such as methanol, ethanol and i-propanol, amides such as dimethylformamide and N-methylpyrrolidone, nitriles such as acetonitrile, amines such as triethylamine, pyridine and N,N-dimethylaniline, halogenated hydrocarbons such as dichloromethane, chlorobenzene and 1,2-dichloromethane, or water. Mixtures of said solvents are also suitable.

Suitable condensation aids are eg. oxalyl chloride carbonyldiimidazole, carbodiimides such as cyclohexylcarbodiimide, halogenating agents such as thionyl chloride, phosphorus oxychloride, phosgene, phosphorus trichloride and phosphorus pentachloride, or methyl or ethyl chloroformate.

The use of a halogenating agent is preferred, an acid halide first being formed in situ, which then reacts further with the hydroxylamine $HN(R^{5'})$—$OR^6$ or $H_2N$—$OR^6$ to give the products II or IV.

There is, however, also the possibility of specifically preparing the acid halide in a separate process step and, if desired in purified form, then reacting it with the hydroxylamine $HN(R^{5'})$—$OR^6$ or $H_2N$—$OR^6$.

Hydroxylamines which are obtainable in the form of their salts, in particular as hydrochlorides, hydrobromides or sulfates, or are obtained during preparation as salts can be liberated by addition of a suitable base before reaction thereof with IX or X, if desired even in the reaction mixture with the condensation aid and IX or X.

Suitable bases for this purpose are, in particular, those mentioned in method a).

The amounts of condensation aid, IX or X and hydroxylamine $HN(R^{5'})$—$OR^6$ or $H_2N$—$OR^6$ are not critical. Expediently, approximately equimolar amounts of the starting substances are used. If desired, the condensation aid can even be employed in an excess, it then being possible to carry out the reaction even without inert solvent.

All processes described above are expediently performed at atmospheric pressure or under the autogenous pressure of the respective reaction mixture.

As a rule, the reaction mixtures are worked up by methods known per se, for example by removing the solvent, partitioning the residue in a mixture of water and a suitable organic solvent and working up the organic phase to the product.

Both the substituted cinnamic oxime derivatives of the formula I and the substituted cinnamic hydroxamide derivatives of the formula II can be obtained during preparation as isomer mixtures which, if desired, can be separated into the pure isomers by the methods customary for this purpose. eg. by means of crystallization or chromatography on an optically active adsorbate. Pure optically active isomers can also be prepared, for example, from corresponding optically active starting materials.

Substituted cinnamic oxime derivatives I and cinnamic hydroxamide derivatives II having C-H acidic substituents can be converted to their alkali metal salts in a manner known per se.

Salts of I or II whose metal ion is not an alkali metal ion can customarily be prepared by double decomposition of the corresponding alkali metal salt in aqueous solution.

Other metal salts such as manganese, copper, zinc, iron, calcium, magnesium and barium salts can be prepared from the sodium salts in a customary manner, just as ammonium and phosphonium salts can be prepared by means of ammonia, phosphonium, sulfonium or sulfoxonium hydroxides.

The compounds I and II and their agriculturally utilizable salts are suitable as herbicides, both as isomer mixtures and in the form of the pure isomers. They can control broad-leaved weeds and grass weeds very effectively in crops such as wheat, rice, maize, soybeans and cotton without noticeably damaging the crop plants.

This effect occurs especially at low application rates.

Depending on the particular application method, the compounds I and II or herbicidal compositions containing them can additionally be employed in a further number of crop plants for eliminating undesired plants. Suitable crops, for example, are the following: *Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, vicia faba, Vitis vinifera, Zea mays.*

Moreover, the compounds I and II can also be employed in crops which have been made substantially resistant to the action of I and II or other herbicides by breeding and/or by means of genetic engineering methods.

In addition, the substituted cinnamic oxime derivatives I and cinnamic hydroxamide derivatives II are also suitable for the desiccation and/or defoliation of plants.

As desiccants, they are in particular suitable for the desiccation of the above-ground parts of crop plants such as potato, rape, sunflower and soybean. Completely mechanized harvesting of these important crop plants is thus made possible.

Of economic interest is also the facilitation of harvesting, which is made possible by the temporally concentrated decrease or reduction in the power of adhesion to the tree in the case of citrus fruits, olives or in the case of other species and varieties of pomes, drupes and indehiscent fruit. The same mechanism, that is the promotion of the formation of separating tissue between fruit or leaf and stem part of the plant is also essential for a highly controllable defoliation of useful plants, in particular cotton.

Additionally, the shortening of the time interval in which the individual cotton plants become ripe leads to an enhanced fiber quality after harvesting.

The compounds I and II or the herbicidal compositions containing them can be applied by spraying, atomizing, dusting, broadcasting or watering, for example in the form of directly sprayable aqueous solutions, powders, suspensions, also high-percentage aqueous, oily or other suspensions or dispersions, emulsions, oil dispersions, pastes, dusting compositions, broadcasting compositions or granules. The application forms depend entirely on the intended uses; in each case if possible, they should guarantee the finest dispersion of the active compounds according to the invention.

Suitable inert auxiliaries for the production of directly sprayable solutions, emulsions, pastes or oil dispersions are essentially: mineral oil fractions of medium to high boiling point such as kerosene and diesel oil, also coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, n-propanol, butanol and cyclohexanol, ketones such as cyclohexanone, strongly polar solvents, eg. amines such as N-methylpyrrolidone and water.

Aqueous application forms can be prepared from emulsion concentrates, dispersions, pastes, wettable powders or water-dispersible granules by addition of water. For the production of emulsions, pastes or oil dispersions, the substances as such or dissolved in an oil or solvent can be homogenized in water by means of wetting agents, adhesives, dispersants or emulsifiers.

However, concentrates consisting of active substance, wetting agents, adhesives, dispersants or emulsifiers and possibly solvents or oil can also be prepared, which are suitable for dilution with water.

Suitable surface-active substances are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl esters, lauryl alcohol polyglycol ether acetate, sorbitol esters, ligninsulfite waste liquors or methylcellulose.

Powder, broadcasting and dusting compositions can be produced by mixing or joint grinding of the active substances with a solid carrier.

Granules, eg. coated, impregnated and homogeneous granules can be produced by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products such as cereal meal, tree bark, wood and nut-shell meal, cellulose powder or other solid carriers.

The concentrations of the active compounds I and II in the ready-to-apply preparations can be varied within wide ranges, for example from 0.01 to 95% by weight, preferably from 0.5 to 90% by weight. The active compounds are in this case normally employed in a purity of from 90% to 100%, preferably from 95% to 100% (according to NMR spectrum).

The following formulation examples illustrate the preparation of such preparations:

I. 20 parts by weight of the compound No. I.01 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring the solution out and finely dispersing it in 100,000 parts by weight of water, an aqueous dispersion is obtained which contains 0.02% by weight of the active compound;

II. 20 parts by weight of the compound No. I.02 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of a 25 castor oil. By pouring the solution into and finely dispersing it in 100,000 parts by weight of water, an aqueous dispersion is obtained which contains 0.02% by weight of the active compound;

III. 20 parts by weight of the compound No. I.05 are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound;

IV. 20 parts by weight of the active compound No. I.08, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel are mixed well and ground in hammer mill. By finely dispersing of the mixture in 20,000 parts by weight of water, a spray liquor is obtained which contains 0.1% by weight of the active compound;

V. 3 parts by weight of the compound No. I.09 are mixed with 97 parts by weight of finely divided kaolin. A dusting composition is obtained in this manner which contains 3% by weight of the active compound;

VI. 20 parts by weight of the active compound No. I.13 are intimately mixed with 2 parts by weight of the calcium salt of dodecylbenzenesulfonic acid, 8 parts by weight of fatty alcohol polyglycol ether, 2 parts by weight of the sodium salt of a phenol-urea-formaldehyde condensate and 68 parts by weight of a paraffinic mineral oil. A stable oily dispersion is obtained.

The application of the active compounds I and II or of the herbicidal compositions can be carried out pre-emergence or post-emergence. If the active compounds are less tolerable to certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The application rates of active compound are, depending on the target to be controlled, time of year and stage of growth from 0.001 to 3.0, preferably from 0.01 to 1 kg/ha of active substance (a.s.).

For widening the spectrum of action and for achieving synergistic effects, the substituted cinnamic oxime derivatives I and the substituted cinnamic hydroxamide derivatives II can be mixed with numerous representatives of other herbicidal or growth-regulating active compound groups and applied together. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolinones, sulfonamides, sulfonylureas, aryloxy- and heteroaryloxyphenoxypropionic acids as well as their salts, esters and amides, inter alia.

It may additionally be of use to mix the compounds I or II, on their own or in combination with other herbicides, additionally with further plant protection compositions and to apply them together, for example with pesticides, compositions against phytopathogenic fungi and against bacteria. Additionally of interest is the miscibility with mineral salt solutions, which are employed for the elimination of nutritional and trace element deficiencies. Non-phytotoxic oils and oil concentrates can also be added.

PREPARATION EXAMPLES

Example 1

3-[4-Chloro-3-(2-chloro-2-(ethoxyaminocarbonyl)ethenyl) phenyl]-2,4-dioxo-1-methyl-6-trifluoromethyl-1,2,3,4-tetrahydropyrimidine (compound No. II.02)

Carbonyldiimidazole (0.9 g) was added to a solution of 3-[3-(2-carboxy-2-chloroethenyl)phenyl]-2,4-dioxo-1-methyl-6-trifluoromethyl-1,2,3,4-tetrahydropyrimidine (2.1 g) in 80 ml of tetrahydrofuran, after which the mixture was stirred at 25° C. for one hour. Ethoxyamine (0.34 g), dissolved in 20 ml of tetrahydrofuran, was then added dropwise. After stirring for five hours, the solvent was removed. The residue was taken up in 150 ml of dichloromethane. The organic phase was washed twice each with 30 ml of water, 30 ml of 10% strength by weight sodium hydrogencarbonate solution and again with 30 ml of water, and finally dried over sodium sulfate and concentrated. After crystallization from petroleum ether, 2.0 g of the product were obtained. M.p.: 86–90° C.

Example 2

3-[4-Chloro-3-(2-chloro-2-methoxyaminocarbonylethenyl) phenyl]-2,4-dioxo-1-methyl-6-trifluoromethyl-1,2,3,4-tetrahydropyrimidine (compound II.01)

Carbonyldiimidazole (0.9 g) was added to a solution of 3-[3-(2-carboxy-2-chloroethenyl)phenyl]-2,4-dioxo-1-methyl-6-trifluoromethyl-1,2,3,4-tetrahydropyrimidine (2.1 g) in 80 ml of tetrahydrofuran, after which the mixture was stirred at 25° C. for one hour. Methoxyamine hydrochloride (1.67 g as a 30% strength by weight aqueous solution) and potassium carbonate (0.83 g), dissolved in 20 ml of tetrahydrofuran, were then added dropwise. After stirring for 5 hours, the solvent was distilled off, after which the residue was taken up in 150 ml of dichloromethane. The organic phase was washed twice with 30 ml each of water, twice with 30 ml each of 10% strength by weight sodium hydrogencarbonate solution and again with 30 ml of water, then dried over sodium sulfate and concentrated. After crystallization using petroleum ether, 1.5 g of the product were obtained; m.p.: 136–141° C.

Example 3

3-[4-Chloro-3-(2-chloro-3-methoximino-3-methoxypropenyl)-phenyl]-2,4-dioxo-1-methyl-6-trifluoromethyl-1,2,3,4-tetrahydropyrimidine (compound I.01) and 3-[4-chloro-3-(2-chloro-2-[methoxymethylaminocarbonyl]ethenyl)phenyl]-2,4-dioxo-1-methyl-6-trifluoromethyl-1,2,3,4-tetrahydropyrimidine (compound II.03)

First potassium carbonate (0.76 g) and then dimethyl sulfate (0.63 g) dissolved in 20 ml of acetone were added to a solution of 3-[4-chloro-3-(2-chloro-2-methoxyaminocarbonylethenyl)-phenyl]-2,4-dioxo-1-methyl-6-trifluoromethyl-1,2,3,4-tetrahydropyrimidine (2.2 g) in 80 ml of acetone. After stirring for 17 hours, further dimethyl sulfate (0.13 g) was added, after which the mixture was stirred again for 17 hours and the solvent was then distilled off. The residue was taken up in 100 ml of dichloromethane, and the organic phase was washed three times with 30 ml each of water, dried over sodium sulfate and concentrated. After purification of the crude product by means of chromatography and crystallization, 1.0 g of 3-[4-chloro-3-(2-chloro-3-methoximino-3-methoxypropenyl)phenyl]-2,4-dioxo-1-methyl-6-trifluoromethyl-1,2,3,4-tetrahydropyrimidine (compound I.01; m.p. 152–157° C.) and 0.4 g of 3-[4-chloro-3-(2-chloro-3-[methoxymethylaminocarbonyl]ethenyl)phenyl]-2,4-dioxo-1-methyl-6-trifluoromethyl-1,2,3,4-tetrahydropyrimidine (compound II.03; m.p.: 121–123° C. ) were obtained.

Example 4

3-[4-Chloro-3-(2-chloro-3-methoximino-3-methoxyethoxypropenyl)-phenyl]-2,4-dioxo-1-methyl-6-trifluoromethyl-1,2,3,4-tetrahydropyrimidine (compound I.03) and 3-[4-chloro-3-(2-methoximino-3-methoxyethoxy) ethynylphenyl]-2,4-dioxo-1-methyl-6-trifluoromethyl-1,2,3,4-tetrahydropyrimidine (compound I.18)

Potassium carbonate (1.4 g) and then methoxyethyl tosylate (2.3 g) dissolved in 5 ml of acetone were added to a solution of 3-[4-chloro-3-(2-chloro-2-methoxyaminocarbonylethenyl)phenyl]-2,4-dioxo-1-methyl-6-trifluoromethyl-1,2,3,4-tetrahydropyrimidine (4.4 g) in a mixture of 10 ml of acetone and 5 ml of 1,2-dimethyltetrahydro-2(1H)-pyrimidinone. After stirring at 25° C. for 2 days, N,N-dimethylaminopyridine (0.2 g) was added to the reaction mixture. After stirring at reflux temperature for hours, the solvent was distilled off, after which the residue was taken up in 150 ml of dichloromethane. The dichloromethane phase was washed three times with 50 ml each of water, dried over sodium sulfate and concentrated. After flash chromatography twice, 0.4 g of 3-[4-chloro-3-(2-chloro-3-methoximino-3-methoxyethoxypropenyl) phenyl]-2,4-dioxo-1-methyl-6-trifluoromethyl-1,2,3,4-tetrahydropyrimidine (compound I.03; m.p. 73–74° C.) and 0.12 g of 3-[4-chloro-3-(2-methoximino-3-methoxyethoxy) ethynylphenyl]-2,4-dioxo-1-methyl-6-trifluoromethyl-1,2,3,4-tetrahydropyrimidine (compound I.18; m.p. 127–129° C.) were obtained.

Example 5

3-[4-Chloro-3-(2-chloro-3-[3-propeneoximino]butenyl) phenyl]-2,4-dioxo-1-methyl-6-trifluoromethyl-1,2,3,4-tetrahydropyrimidine (compound I.06)

Sodium carbonate (0.69 g) and 0-3-propenylhydroxylamine hydrochloride (0.66 g) were added to a solution of 3-[4-chloro-3-(2-chloro-3-oxo-butenyl) phenyl]-2,4-dioxo-1-methyl-6-trifluoromethyl-1,2,3,4-tetrahydropyrimidine (2.04 g) in 100 ml of toluene. After stirring at 25° C. for 5 hours, the mixture was refluxed for a further 20 hours, altogether a further 0.53 g of sodium carbonate and 0.55 g of O-3-propenylhydroxylamine hydrochloride being added. The organic phase was then washed three times with 50 ml each of water, dried over sodium sulfate and concentrated. After crystallization, 1.0 g of the product was obtained; m.p.: 73–74° C.

Example 6

3-[3-(3-Acetoxy-2-chloro-3-methoximinopropenyl)-4-chlorophenyl]-2,4-dioxo-1-methyl-6-trifluoromethyl-1,2,3,4-tetrahydropyrimidine (compound I.12) and 3-[3-(2-acetylmethoxyaminocarbonyl-2-chloroethenyl)phenyl]-2,4-dioxo-1-methyl-6-trifluoromethyl-1,2,3,4-tetrahydropyrimidine (compound II.05).

A solution of acetyl chloride (0.39 ml) in 20 ml of dichloromethane was added dropwise at 25° C. to a solution of 3-[4-chloro-3-(2-chloro-3-methoxyaminocarbonylethenyl)phenyl]-2,4-dioxo-1-methyl-6-trifluoromethyl-1,2,3,4-tetrahydropyrimidine (2.2 g) and triethylamine (0.77 ml) in 80 ml of dichlormethane. After stirring at about 20° C. for 20 hours, the organic phase was washed three times with 30 ml each of water, then dried and concentrated. The crude product was purified by chromatography (eluent: dichloromethane/ethyl acetate=9:1).

Yield: 1.1 g of 3-[3-(3-acetoxy-2-chloro-3-methoximinopropenyl)-4-chlorophenyl]-2,4-dioxo-1-methyl-6-trifluoromethyl-1,2,3,4-tetrahydropyrimidine (m.p.: 158–160° C.) and 0.2 g of 3-[3-(2-[acetylmethoxyaminocarbonyl]-2-chloroethenyl)phenyl]-2,4-dioxo-1-methyl-6-trifluoromethyl-1,2,3,4-tetrahydropyrimidine (m.p.: 117–118° C).

Example 7

3-[3-(3-Bromo-2-chloro-3-methoximinopropenyl)-4-chlorophenyl]-2,4-dioxo-1-methyl-6-trifluoromethyl-1,2,3,4-tetrahydropyrimidine (compound I.13).

Tetrabromomethane (5.0 g) was added to a solution of 3-[4-chloro-3-(2-chloro-2-methoxyaminocarbonylethenyl) phenyl]-2,4-dioxo-1-methyl-6-trifluoromethyl-1,2,3,4-tetrahydropyrimidine (4.4 g) and triphenylphosphine (3.9 g) in 100 ml of acetonitrile. The mixture was then refluxed for 35 hours, during which triphenylphosphine (6.5 g) and tetrabromomethane (8.3 g) were added twice. After cooling the reaction mixture, the solvent was removed. The residue was purified by chromatography (eluent: dichloromethane). Yield: 3.0 g; m.p.: 128–130° C.

Example 8

3-[4-Chloro-3-(2-chloro-3-ethylthio-2-methoximinopropenyl)-phenyl]-2,4-dioxo-1-methyl-6-trifluoromethyl-1,2,3,4-tetrahydropyrimidine (compound I.19)

A solution of ethylmercaptan (0.34 g) in 20 ml of tetrahydrofuran was added under nitrogen to a suspension of sodium hydride (0.18 g; 80% strength by weight in white oil) in 100 ml of tetrahydrofuran. After stirring for 30 minutes, the mixture was treated with a solution of 3-[3-(3-bromo-2-chloro-3-methoximinopropenyl)-4-chlorophenyl]-2,4-dioxo-1-methyl-6-trifluoromethyl-1,2,3,4-tetrahydropyrimidine (2.5 g; prepared according to Example 7) in 30 ml of tetrahydrofuran. The mixture was then stirred for 20 hours, after which further ethylmercaptan (0.34 g) and sodium hydride (0.34 g; 80% strength in white oil) were added. The mixture was then stirred for a further 20 hours. For working up, the reaction mixture was added to 150 ml of water. The product was extracted from the aqueous phase with dichloromethane (twice 100 ml each). The combined organic phases were washed three times with 50 ml each of water, dried over sodium sulfate and concentrated. The crude product was purified by chromatography.

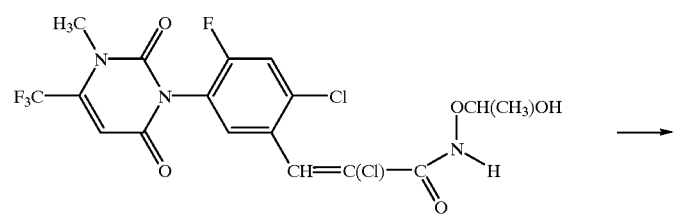

-continued

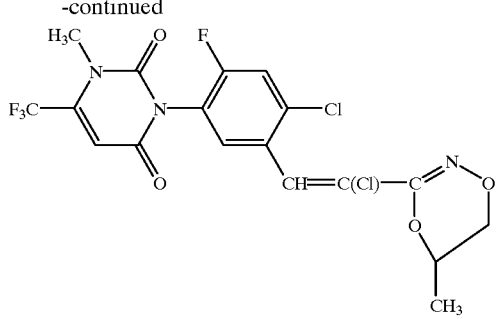

0.0048 mol of dimethyl sulfate in 20 ml of acetone was slowly added dropwise at about 25° C. to a mixture of 0.004 mol of 3-[4-chloro-3-(2-chloro-2-[(1-hydroxyethoxy)aminocarbonyl]-ethenyl)-2-fluorophenyl]-2,4-dioxo-1-methyl-6-trifluoromethyl-1,2,3,4-tetrahydropyrimidine, 0.0048 mol of potassium carbonate and 80 ml of acetone. The mixture was subsequently stirred for 12 hours and then concentrated. The residue was taken up in 100 ml of methylene chloride, after which the methylene chloride phase was washed 3 times with 30 ml of water each time, then dried over sodium sulfate and finally concentrated. The crude product was purified by chromatography on silica gel (eluent: dichloromethane). Yield: 0,25 g.

The abovementioned compounds together with further substituted cinnamic oxime derivatives I which were prepared or can be prepared in a similar manner are listed in the following Tables 3 to 5:

TABLE 3

$$\left\{\begin{array}{l} R^1 = Cl; \\ Cyc = 1\text{-}CH_3, \\ 6\text{-}CF_3\text{-}uracil\text{-}3\text{-}yl \end{array}\right\}$$

| No. | $R^2$ | $R^3$ | $R^4$ | Y | $R^5$ | $R^6$ | M.p. [° C.] |
|---|---|---|---|---|---|---|---|
| I.01 | H | H | Cl | —O— | $CH_3$ | $CH_3$ | 152–157 |
| I.02 | H | H | Cl | —O— | $CH_3$ | $C_2H_5$ | 136–141 |
| I.03 | H | H | Cl | —O— | $(CH_2)_2OCH_3$ | $CH_3$ | 73–74 |
| I.04 | H | H | Cl | —O— | $CH(CH_3)_2$ | $CH_3$ | 91–93 |
| I.05 | H | H | Cl | —O— | $(CH_2)_2$—$CH_2F$ | $CH_3$ | 133–136 |
| I.06 | H | H | Cl | — | $CH_3$ | $CH_2CH=CH_2$ | 72–74 |
| I.07 | H | H | H | — | $CH_3$ | $CH_3$ | 183–184 |
| I.08 | H | H | H | — | $CH_3$ | $CH_2$—CN | 204–205 |
| I.09 | H | H | Cl | —O— | $C_2H_5$ | $CH_3$ | 125–127 |
| I.10 | H | H | Cl | —O— | $CH(CH_3)$—$COOCH_3$ | $CH_3$ | oil |
| I.11 | H | H | Cl | —O— | $CH_2CO$-(azepin-1-yl) | $CH_3$ | 58–63 |
| I.12 | H | H | Cl | —O—CO— | $CH_3$ | $CH_3$ | 158–160 |
| I.13 | H | H | Cl | — | Br | $CH_3$ | 128–130 |
| I.14 | H | H | Cl | —O—CO— | $CH_2Cl$ | $CH_3$ | 144–148 |
| I.15 | H | H | H | — | H | $CH_2$—$C_2H_5$ | 158–161 |
| I.16 | H | H | $CH_3$ | — | H | $CH_3$ | 148–149 |
| I.17 | H | H | $CH_3$ | — | H | $CH_2CH=CH_2$ | 72–74 |
| I.18 | H | chemical bond | — | $CH_2CH_2$—$OCH_3$ | $CH_3$ | 127–129 |
| I.19 | H | H | Cl | —S— | $C_2H_5$ | $CH_3$ | 103–105 |
| I.20 | H | H | Cl | —S— | $CH_2COOCH_3$ | $CH_3$ | oil |
| I.21 | H | H | Cl | —O— | $CH_3$ | $CH_2$—$C_6H_5$ | 112–114 |
| I.22 | H | H | Cl | —O— | $CH_3$ | $CH_2$—$CH=CH_2$ | 93–98 |
| I.23 | H | H | Cl | —O—$SO_2$— | $CH_3$ | $CH_3$ | 78–82 |
| I.24 | H | H | Cl | —O— | $CH_3$ | $CH(CH_3)COOC_2H_5$ | 119–121 |
| I.25 | H | H | Cl | —O— | $CH_3$ | $CH_2$—$CH(CH_3)$—OH | oil |

TABLE 3-continued

Structure: I with R¹ = Cl; Cyc = 1-CH₃, 6-CF₃-uracil-3-yl

| No. | R² | R³ | R⁴ | Y | R⁵ | R⁶ | M.p. [° C.] |
|---|---|---|---|---|---|---|---|
| I.26 | F | H | Cl | —O— | CH₃ | CH₃ | 133–135 |
| I.27 | F | H | Cl | —O— | CH(CH₃)COOCH₃ | CH₃ | oil |
| I.28 | F | H | Cl | —O— | —CH(CH₃)—CH₂— | | 84–87 |
| I.29 | F | H | Cl | —O— | CH₃ | CH₂CH(CH₃)OH | 68–70 |
| I.30 | F | H | Cl | —O— | CH₃ | CH₂COOC₂H₅ | oil |
| I.31 | F | H | Cl | —O— | CH₃ | CH(CH₃)COOC₂H₅ | oil |
| I.32 | H | H | Cl | —O— | —CH(CH₃)CH₂— | | 176–178 |

TABLE 4

II {R¹ = Cl; R³, R⁹ = H; X¹, X² = O}

| No. | R² | R⁴ | Y' | R⁵' | R⁶ | M.p. [° C.] |
|---|---|---|---|---|---|---|
| II.01 | H | Cl | O | H | CH₃ | 136–141 |
| II.02 | H | Cl | O | H | C₂H₅ | 81–110 |
| II.03 | H | Cl | O | CH₃ | CH₃ | 121–123 |
| II.04 | H | Cl | O | CH₃ | C₂H₅ | 105–108 |
| II.05 | H | Cl | O | CO—CH₃ | CH₃ | 117–118 |
| II.06 | H | Cl | O | C₂H₅ | CH₃ | 128–130 |
| II.07 | H | Cl | O | H | CH(CH₃)—CO—OC₂H₅ | 52–55 |
| II.08 | H | Cl | O | H | CH₂—C₆H₅ | 58–62 |
| II.09 | H | Cl | O | CH₃ | CH₂—C₆H₅ | 93–96 |
| II.10 | H | Cl | O | H | CH₂—CH=CH₂ | 68–70 |
| II.11 | H | Cl | O | CH₃ | CH₂—CH=CH₂ | 87–91 |
| II.12 | H | Cl | O | H | CH₂—CH(CH₃)—OH | 76–79 |
| II.13 | H | Cl | O | H | CH₂CH₂—C₂H₅ | oil |
| II.14 | F | Cl | O | H | CH₃ | |
| II.15 | F | Cl | O | CH₃ | CH₃ | 130–140 |
| II.16 | F | Cl | O | H | CH₂CH=CH₂ | oil |
| II.17 | F | Cl | O | CH₃ | CH₂CH=CH₂ | oil |
| II.18 | F | Cl | O | H | CH₂—H(CH₃)OH | 157–158 |
| II.19 | F | Cl | O | CH₃ | CH₂—COOC₂H₅ | oil |
| II.20 | F | Cl | O | H | CH(CH₃)—COOC₂H₅ | oil |
| II.21 | F | Cl | O | CH₃ | CH(CH₃)—COOC₂H₅ | oil |
| II.22 | H | Cl | O | CH₃ | CH(CH₃)—COOC₂H₅ | oil |

TABLE 5

I {R¹ = Cl; R³ = H; Cyc = N-(3,4,5,6-Tetrahydrophthalimido)}

| No. | R² | R⁴ | Y | R⁵ | R⁶ | M.p. [° C.] |
|---|---|---|---|---|---|---|
| I.101 | H | Cl | — | H | CH₃ | 84–90 |
| I.102 | H | Cl | — | H | CH₂CH=CH₂ | 95–98 |
| I.103 | H | Cl | — | H | C₂H₅ | 128–136 |
| I.104 | H | Cl | — | H | CH₂COOH | 105–120 |
| I.105 | H | CH₃ | — | H | CH₃ | 67–68 |
| I.106 | H | CH₃ | — | H | C₂H₅ | oil |
| I.107 | H | CH₃ | — | H | CH₂COOCH₃ | 94–95 |
| I.108 | H | CH₃ | — | H | H | 148–150 |
| I.109 | H | H | — | COOCH₃ | CH₃ | 140–141 |
| I.110 | F | H | — | H | n-C₃H₇ | oil |
| I.111 | H | Cl | —O— | CH₃ | CH₃ | 150–153 |

Use examples (herbicidal activity)

It was possible to show the herbicidal action of the substituted cinnamic oxime derivatives of the formula I and of the substituted cinnamic hydroxamide derivatives of the formula II by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth, and then covered with transparent plastic hoods until the plants had taken root. This covering causes uniform germination of the test plants if this has not been adversely affected by the active compounds.

For the purpose of post-emergence treatment, the test plants were first raised, depending on growth form, up to a growth height of from 3 to 15 cm, and only then treated with the active compounds suspended or emulsified in water. For this purpose, the test plants were either sown directly and cultivated in the same containers or they were first raised separately as seedlings and transplanted into the test containers a few days before treatment. The application rate for post-emergence treatment was 0.0313 or 0.0156 kg of active substance per hectare.

The plants were kept in a species-specific manner at 10–25° C. or 20–35° C. The test period extended over 2 to 4 weeks. During this time, the plants were tended and their reaction to the individual treatments was evaluated.

Assessment was carried out on a scale from 0 to 100. 100 in this case means no emergence of the plants or complete destruction at least of the above-ground parts and 0 means no damage or normal course of growth.

The plants used in the greenhouse tests consist of the following species:

| Latin name | Common name |
| --- | --- |
| Abutilon theophrasti | velvetleaf |
| Ipomoea subspecies | morning-glory |
| Polygonum pensylvanicum | smartweed |
| Solanum nigrum | black nightshade |
| Veronica subspecies | speedwell |

Post-emergence, harmful plants were very well controlled using the compounds of Examples I.01 and I.103 at 0.0313 and 0.0156 kg/ha of active substance.

Use examples for the desiccant/defoliant activity of compounds I and II The test plants used were young, 4-leaved (without seed leaves) cotton plants, which were raised under greenhouse conditions (rel. atmospheric humidity 50 to 70%; day/night temperature 7/20° C.).

The young cotton plants were subjected to foliar treatment until dripping wet with aqueous preparations of the active compounds (with addition of 0.15% by weight of the fatty alcohol alkoxylate Plurafac LF 700, based on the spray liquor). The amount of water applied was the equivalent of 1000 l/ha. After 13 days, the number of leaves shed and the degree of defoliation was determined in %.

In the case of the untreated control plants, no leaf fall occurred.

We claim:

1. A cinnamic oxime compound of the formula I

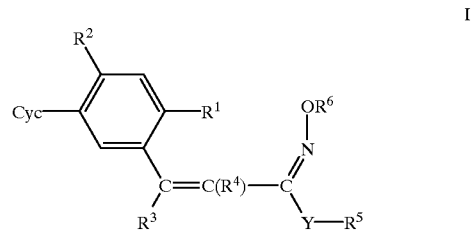

where the variables have the following meanings:

$R^1$ is halogen, nitro, cyano, or trifluoromethyl;

$R^2$ is hydrogen or halogen;

$R^3$ is hydrogen, halogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl or hydroxy-$C_1$–$C_6$-alkyl;

$R^4$ is hydrogen, halogen, cyano, $C_1$–$C_6$-alkyl, $C_1$–$C_6$-haloalkyl, or $R^3$ and $R^4$ together are a chemical bond;

Y is oxygen, sulfur, oxycarbonyl, oxysulfonyl or a chemical bond;

$R^5$ is $C_1$–$C_6$-alkyl or $C_1$–$C_6$-haloalkyl, where these groups are unsubstituted or carry one of the following radicals: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy or a 3- to 7-membered azaheterocycle N-bonded to said $C_1$–$C_6$-alkyl or $C_1$–$C_6$-haloalkyl via a carbonyl bridge and which, in addition to carbon ring members, can also contain an oxygen or a sulfur atom as a ring member; is $C_3$–$C_6$-cycloalkyl, $C_3$–$C_6$-alkenyl, $C_3$–$C_6$-alkynyl, phenyl or phenyl-$C_1$–$C_6$-alkyl, where the phenyl rings are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl; or, if Y is a chemical bond, is additionally hydrogen or halogen; $R^6$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkoxy) carbonyl-$C_1$–$C_6$-alkyl, ($C_1$–$C_6$-alkyl)carbonyl-$C_1$–$C_6$-alkyl, ($C_1$–$C_6$-alkyl)carbonyloxy-$C_1$–$C_6$-alkyl or phenyl-$C_1$–$C_6$-alkyl, where the phenyl ring is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl; or, if Y is oxygen or sulfur, $R^5$ and $R^6$ together are a $C_1$–$C_3$-alkylene chain which can carry a $C_1$–$C_6$-alkyl substituent;

Cyc is N-(3,4,5,6-tetraphydrophthalimido) or a radical

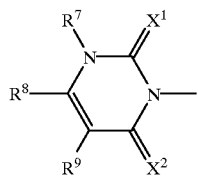

$X^1$ and $X^2$ independently of one another being oxygen or sulfur;

$R^7$ being hydrogen, $C_1$–$C_6$-alkyl, $C_1$–$C_6$-haloalkyl or amino, and $R^8$ and $R^9$ independently of one another being hydrogen, halogen, $C_1$–$C_6$-alkyl, $C_1$–$C_6$-haloalkyl or phenyl, which is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

or an agriculturally utilizable salt of the compound I.

2. A cinnamic hydroxamide compound of the formula II

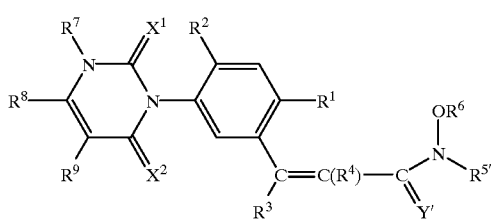

where the variables have the following meanings:

$R^1$ is halogen, nitro, cyano, or trifluoromethyl;

$R^2$ is hydrogen or halogen;

$R^3$ is hydrogen, halogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl or hydroxy-$C_1$–$C_6$-alkyl;

$R^4$ is hydrogen, halogen, cyano, $C_1$–$C_6$-alkyl, $C_1$–$C_6$-haloalkyl, or $R^3$ and $R^4$ together are a chemical bond;

$R^{5'}$ is $C_1$–$C_6$-alkyl or $C_1$–$C_6$-haloalkyl, where these groups are unsubstituted or carry one of the following radicals: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy or a 3- to 7-membered azaheterocycle N-bonded to said $C_1$–$C_6$-alkyl or $C_1$–Cr-haloalkyl via a carbonyl bridge and which, in addition to carbon ring members, can also contain an oxygen or a sulfur atom as a ring member;

is $C_3$–$C_6$-cycloalkyl, $C_3$–$C_6$-alkenyl, $C_3$–$C_6$-alkynyl, ($C_1$–$C_6$-alkyl)carbonyl, ($C_1$–$C_6$-haloalkyl)carbonyl, ($C_1$–$C_6$-alkoxy)carbonyl, phenyl or phenyl-$C_1$–$C_6$-alkyl, where the phenyl rings are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^6$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkoxy) carbonyl-$C_1$–$C_6$-alkyl, ($C_1$–$C_6$-alkyl)carbonyl-$C_1$–$C_6$-alkyl, ($C_1$–$C_6$-alkyl)carbonyloxy-$C_1$–$C_6$-alkyl or phenyl-$C_1$–$C_6$-alkyl, where the phenyl ring is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

Y', $X^1$ and $X^2$ independently of one another are oxygen or sulfur;

$R^7$ is hydrogen, $C_1$–$C_6$-alkyl, $C_1$–$C_6$-haloalkyl or amino, and $R^8$ and $R^9$ independently of one another are hydrogen, halogen, $C_1$–$C_6$-alkyl, $C_1$–$C_6$-haloalkyl or phenyl which is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

or an agriculturally utilizable salt of the compound II.

3. A herbicidal composition, which comprises a herbicidally active amount of a cinnamic oxime compound of the formula I, or an agriculturally utilizable salt of I, as defined in claim 1 and an inert or solid carrier and optionally an adjuvant.

4. A herbicidal composition, which comprises a herbicidally active amount of a cinnamic hydroxamide compound of the formula II or an agriculturally utilizable salt of II, as defined in claim 2, and an inert or solid carrier and optionally an adjuvant.

5. A composition for the desiccation or defoliation of plants, which comprises an amount of a cinnamic oxime compound of the formula I or an agriculturally utilizable salt of I, as defined in claim 1, having desiccant or defoliant activity and an inert or solid carrier and optionally an adjuvant.

6. A composition for the desiccation or defoliation of plants, which comprises an amount of a cinnamic hydroxamide compound of the formula II or an agriculturally utilizable salt of II, as defined in claim 2, having desiccant or defoliant activity and an inert or solid carrier and optionally an adjuvant.

7. A process for preparing herbicidally active compositions, which comprises mixing a herbicidally active amount of a cinnamic oxime compound of the formula I or an agriculturally utilizable salt of I, as defined in claim 1, and an inert liquid or solid carrier and optionally an adjuvant.

8. A process for preparing compositions having desiccant or defoliant activity, which comprises mixing an amount of a cinnamic oxime compound of the formula I or an agriculturally utilizable salt of I, as defined in claim 1, having desiccant/defoliant activity and an inert liquid or solid carrier and optionally an adjuvant.

9. A process for preparing herbicidally active compositions, which comprises mixing a herbicidally active amount of a cinnamic hydroxamide compound of the formula II or an agriculturally utilizable salt of II, as defined in claim 2, and an inert liquid or solid carrier and optionally an adjuvant.

10. A process for preparing compositions having desiccant or defoliant activity, which comprises mixing an amount of cinnamic hydroxamide compound of the formula II an agriculturally utilizable salt of II, as defined in claim 2, having desiccant/defoliant activity and an inert liquid or solid carrier and optionally an adjuvant.

11. A method of controlling undesired plant growth, which comprises allowing a herbicidally active amount of a cinnamic oxime compound of the formula I or of an agriculturally utilizable salt of I, as defined in claim 1, to act on the plants, their habitat or on seed.

12. A method for the desiccation or defoliation of plants, which comprises allowing an amount of a cinnamic oxime compound of the formula I or of an agriculturally utilizable salt of I, as defined in claim 1, having defoliant or desiccant activity to act on plants.

13. A method of controlling undesired plant growth, which comprises allowing a herbicidally active amount of a cinnamic hydroxamide compound of the formula II or of an agriculturally utilizable salt of II, as defined in claim 2, to act on the plants, their habitat or on seed.

14. A method for the desiccation or defoliation of plants, which comprises allowing an amount of a cinnamic hydroxide compound of the formula II or of an agriculturally utilizable salt of II, as defined in claim 2, having defoliant or desiccant activity to act on plants.

15. A method as defined in claim 14, wherein cotton is treated.

16. A method as defined in claim 15, wherein cotton is treated.

17. A cinnamic oxime of the formula VIII

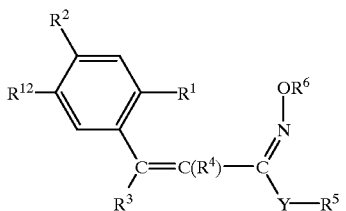

VIII wherein
$R^1$ is halogen, nitro, cyano, or trifluoromethyl;
$R^2$ is hydrogen or halogen:
$R^3$ is hydrogen, halogen, $C_1$–$C_6$-alkyl, $C_1$–$C_6$-haloalkyl, $C_3$–$C_6$-cycloalkyl, $C_1$–$C_6$-alkenyl, $C_3$–$C_6$-alkynyl or hydroxy-$C_1$–$C_6$-alkyl;

$R^4$ is hydrogen, halogen, cyano, $C_1$–$C_6$-alkyl, $C_1$–$C_6$-haloalkyl, or $R^3$ and $R^4$ together are a chemical bond;

$R^5$ is $C_1$–$C_6$-alkyl or $C_1$–$C_6$-haloalkyl, where these groups are unsubstituted or carry one of the following radicals: hydroxyl, cyano, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy or a 3- to 7-membered azaheterocycle N-bonded to said $C_1$–$C_6$-alkyl or $C_1$–$C_6$-haloalkyl via a carbonyl bridge and which, in addition to carbon ring members, can also contain an oxygen or a sulfur atom as a ring member;

is $C_3$–$C_6$-cycloalkyl, $C_3$–$C_6$-alkenyl, $C_3$–$C_6$-alkynyl, phenyl or phenyl-$C_1$–$C_6$-alkyl, where the phenyl rings are unsubstituted or carry one to three substituents selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl; or, if Y is a chemical bond. is additionally hydrogen or halogen;

$R^6$ is hydrogen, $C_1$–$C_6$-alkyl, $C_1$–$C_6$-haloalkyl. $C_3$–$C_6$-cycloalkyl, $C_3$–$C_6$-alkenyl, $C_3$–$C_6$-alkynyl, hydroxy-$C_1$–$C_6$-alkyl, $C_1$–$C_6$-alkoxy-$C_1$–$C_6$-alkyl, $C_1$–$C_6$-alkylthio-$C_1$–$C_6$-alkyl, cyano-$C_1$–$C_6$-alkyl, ($C_1$–$C_6$-alkoxy)carbonyl-$C_1$–$C_6$-alkyl, ($C_1$–$C_6$-alkyl)carbonyl-$C_1$–$C_6$-alkyl, ($C_1$–$C_6$-alkyl)carbonyloxy-$C_1$–$C_6$-alkyl or phenyl-$C_1$–$C_6$-alkyl, where the phenyl ring is unsubstituted or carries one to three substituents selected from the group consisting of cyano, nitro, halogen, $C_1$–$C_6$-alkyl, $C_1$–$C_6$-haloalkyl, $C_1$–$C_6$-alkoxy and ($C_1$–$Cr$-alkoxy)carbonyl; or, if Y is oxygen or sulfur, $R^5$ and $R^6$ together are a $C_1C_3$-alkylene chain which can carry a $C_1$–$C_6$-alkyl substituent; and $R^{12}$ is nitro, amino, isocyanato, isothiocyanato, ($C_1$–$C_6$-alkyl)carbamato or phenylcarbamato.

* * * * *

UNITED STATES PATENT AND TRADEMARK OFFICE
CERTIFICATE OF CORRECTION

PATENT NO. : 6,013,606
DATED : January 11, 2000
INVENTOR(S) : Klintz et al.

It is certified that error appears in the above-identified patent and that said Letters Patent is hereby corrected as shown below:

Column 37, claim 1,
Line 51, "$C_1$-Cr-haloalkyl" should be -- $C_1$-$C_6$-haloalkyl --.

Column 38, claim 3,
Line 21, after "inert" insert -- liquid --.

Column 38, claim 4,
Line 26, after "inert" insert -- liquid --.

Column 38, claim 5,
Line 33, after "inert" insert -- liquid --.

Column 38, claim 6,
Line 39, after "inert" insert -- liquid --.

Column 38, claim 10,
Line 64 insert -- a -- before -- cinnamic --.

Column 39, claim 11,
Line 5, "t heir" should be -- their --.

Column 39, claim 14,
Line 17, "al owing" should be -- allowing --.

Column 39, claim 15,
Line 21, "claim 14" should be -- claim 12 --.

Column 39, claim 16,
Line 23, "claim 15" should be -- claim 14 --.

Column 39, claim 17,
Line 42, "$C_1$-$C_6$-alkenyl" should be -- $C_3$-$C_6$-alkenyl --.

UNITED STATES PATENT AND TRADEMARK OFFICE
CERTIFICATE OF CORRECTION

PATENT NO. : 6,013,606
DATED : January 11, 2000
INVENTOR(S) : Klintz et al.

It is certified that error appears in the above-identified patent and that said Letters Patent is hereby corrected as shown below:

Column 40, claim 17,
Line 35, "$C_1$-Cr-alkoxy" should be -- $C_1$-$C_6$-alkoxy --.

Signed and Sealed this

Fourth Day of December, 2001

Attest:

NICHOLAS P. GODICI
*Attesting Officer*   *Acting Director of the United States Patent and Trademark Office*